(12) United States Patent
Karasic et al.

(10) Patent No.: US 10,010,316 B2
(45) Date of Patent: *Jul. 3, 2018

(54) FLEXIBLE ANCHOR DELIVERY SYSTEM

(71) Applicant: Smith & Nephew, Inc., Memphis, TN (US)

(72) Inventors: Geoffrey I. Karasic, Milton, MA (US); Brett A. McKenzie, Brighton, MA (US); Steven William Astorino, Norfolk, MA (US); Richard M. Lunn, Kingston, MA (US); Matthew Edwin Koski, Westford, MA (US); Tatsuya Arai, League City, TX (US); Mark Edwin Housman, North Attleboro, MA (US); Roland F. Gatturna, Bourne, MA (US)

(73) Assignee: Smith & Nephew, Inc., Memphis, TN (US)

( * ) Notice: Subject to any disclaimer, the term of this patent is extended or adjusted under 35 U.S.C. 154(b) by 456 days.

This patent is subject to a terminal disclaimer.

(21) Appl. No.: 14/666,017

(22) Filed: Mar. 23, 2015

(65) Prior Publication Data

US 2015/0190131 A1 Jul. 9, 2015

Related U.S. Application Data

(63) Continuation of application No. 13/654,855, filed on Oct. 18, 2012, now Pat. No. 8,986,327.

(51) Int. Cl.
  *A61B 17/04* (2006.01)
  *A61B 17/16* (2006.01)
  *A61B 17/06* (2006.01)

(52) U.S. Cl.
  CPC ...... *A61B 17/0401* (2013.01); *A61B 17/1633* (2013.01); *A61B 17/06166* (2013.01);
  (Continued)

(58) Field of Classification Search
  CPC ............ A61B 17/0482; A61B 17/0469; A61B 17/0483; A61B 17/1633;
  (Continued)

(56) References Cited

U.S. PATENT DOCUMENTS 3,580,256 A 5/1971 Wilkinson
4,605,414 A 8/1986 Czajka
(Continued)

FOREIGN PATENT DOCUMENTS

CN 101888810 A 11/2010
EP 0328401 A1 8/1989
(Continued)

OTHER PUBLICATIONS

Office Action from related Russian Application No. 2014136769/14(059452) dated Dec. 30, 2017.
(Continued)

*Primary Examiner* — Christopher L Templeton
*Assistant Examiner* — George J Ulsh
(74) *Attorney, Agent, or Firm* — Burns & Levinson, LLP; Joseph M. Maraia

(57) ABSTRACT

An assembly includes a flexible fixation member, a suture, and a delivery device. The flexible fixation member includes a body with two terminal ends. A suture passes through the flexible fixation member at various points along a length of the body such that portions of the fixation member are slidable relative to the suture and configurable to form a cluster within a surgical site. The delivery device includes a tubular member, an elongated inserter, and a trigger. The elongated inserter is slidably disposed within the tubular member. The inserter has a forked distal end configured to receive a portion of the flexible fixation member and the suture. The trigger is finger-engagable and fixedly coupled to the proximal end of the inserter. It is configured to
(Continued)

advance and retract the inserter relative to the tubular member. The trigger includes a retention member for retaining a proximal end portion of the suture.

16 Claims, 32 Drawing Sheets

(52) U.S. Cl.
CPC . *A61B 2017/042* (2013.01); *A61B 2017/0406* (2013.01); *A61B 2017/047* (2013.01); *A61B 2017/0409* (2013.01); *A61B 2017/0446* (2013.01); *A61B 2017/0454* (2013.01); *A61B 2017/0462* (2013.01); *A61B 2017/0496* (2013.01)

(58) Field of Classification Search
CPC .... A61B 2017/0406; A61B 2017/0409; A61B 2017/0454; A61B 2017/0462; A61B 2017/0496; A61B 17/06166; A61B 2017/042; A61B 2017/0446; A61B 2017/047
USPC ........ 606/232, 144, 139, 148, 98; 623/13.11
See application file for complete search history.

(56) References Cited

U.S. PATENT DOCUMENTS

| | | |
|---|---|---|
| 5,217,470 A | 6/1993 | Weston |
| 5,234,445 A | 8/1993 | Walker et al. |
| 5,306,301 A | 4/1994 | Graf et al. |
| 5,405,352 A | 4/1995 | Weston |
| 5,449,367 A | 9/1995 | Kadry |
| 5,451,203 A | 9/1995 | Lamb |
| 5,527,341 A | 6/1996 | Gogolewski et al. |
| 5,645,588 A | 7/1997 | Graf et al. |
| 5,690,649 A | 11/1997 | Li |
| 5,718,717 A | 2/1998 | Bonutti |
| 5,769,894 A | 6/1998 | Ferragamo |
| 5,893,592 A | 4/1999 | Schulze et al. |
| 5,989,252 A | 11/1999 | Fumex |
| 6,143,029 A | 11/2000 | Rippstein |
| 6,193,754 B1 | 2/2001 | Seedhom |
| 6,296,659 B1 | 10/2001 | Foerster |
| 6,517,578 B2 | 2/2003 | Hein |
| 7,390,329 B2 | 6/2008 | Westra et al. |
| 7,390,332 B2 | 6/2008 | Selvitelli et al. |
| 7,601,165 B2 | 10/2009 | Stone |
| 7,658,751 B2 | 2/2010 | Stone et al. |
| 7,736,378 B2 | 6/2010 | Maahs et al. |
| 7,749,250 B2 | 7/2010 | Stone et al. |
| 7,771,455 B2 | 8/2010 | Ken |
| 7,905,903 B2 | 3/2011 | Stone et al. |
| 7,905,904 B2 | 3/2011 | Stone et al. |
| 7,909,851 B2 | 3/2011 | Stone et al. |
| 7,959,650 B2 | 6/2011 | Kaiser et al. |
| 7,972,292 B2 | 7/2011 | Behl et al. |
| 8,057,511 B2 | 11/2011 | Flores et al. |
| 8,088,130 B2 | 1/2012 | Kaiser et al. |
| 8,118,836 B2 | 2/2012 | Denham et al. |
| 8,128,640 B2 | 3/2012 | Harris et al. |
| 8,128,658 B2 | 3/2012 | Kaiser et al. |
| 8,137,382 B2 | 3/2012 | Denham et al. |
| 8,172,871 B2 | 5/2012 | Ken |
| 8,241,305 B2 | 8/2012 | Stone |
| 8,298,262 B2 | 10/2012 | Stone et al. |
| 8,303,604 B2 | 11/2012 | Stone et al. |
| 8,308,765 B2 | 11/2012 | Saadat et al. |
| 8,361,113 B2 | 1/2013 | Stone et al. |
| 8,409,253 B2 | 4/2013 | Stone et al. |
| 2001/0002440 A1 | 5/2001 | Bonutti |
| 2001/0041938 A1 | 11/2001 | Hein |
| 2002/0029066 A1 | 3/2002 | Foerster |
| 2002/0115999 A1 | 8/2002 | McDevitt et al. |
| 2003/0050666 A1 | 3/2003 | Grafton |
| 2003/0149448 A1 | 8/2003 | Foerster et al. |
| 2004/0133238 A1 | 7/2004 | Cerier |
| 2004/0181234 A1 | 9/2004 | McDevitt et al. |
| 2004/0220573 A1 | 11/2004 | McDevitt et al. |
| 2005/0033364 A1 | 2/2005 | Gregoire et al. |
| 2005/0149118 A1 | 7/2005 | Koyfman et al. |
| 2005/0187577 A1 | 8/2005 | Selvitelli et al. |
| 2005/0209622 A1 | 9/2005 | Carrison |
| 2005/0251159 A1 | 11/2005 | Ewers et al. |
| 2005/0277985 A1 | 12/2005 | Wert et al. |
| 2006/0155328 A1 | 7/2006 | Foerster |
| 2006/0178680 A1 | 8/2006 | Nelson et al. |
| 2006/0229671 A1 | 10/2006 | Steiner et al. |
| 2006/0259076 A1 | 11/2006 | Burkhart et al. |
| 2006/0293709 A1 | 12/2006 | Bojarski et al. |
| 2007/0010857 A1 | 1/2007 | Sugimoto et al. |
| 2007/0016244 A1 | 1/2007 | Behl et al. |
| 2007/0156174 A1 | 7/2007 | Kaiser et al. |
| 2007/0185532 A1 | 8/2007 | Stone et al. |
| 2007/0239209 A1 | 10/2007 | Fallman |
| 2008/0065114 A1 | 3/2008 | Stone et al. |
| 2008/0140092 A1 | 6/2008 | Stone et al. |
| 2008/0140093 A1 | 6/2008 | Stone et al. |
| 2008/0188893 A1 | 8/2008 | Selvitelli et al. |
| 2008/0208204 A1 | 8/2008 | Schmieding et al. |
| 2008/0208252 A1 | 8/2008 | Holmes |
| 2008/0255557 A1 | 10/2008 | Koyfman et al. |
| 2008/0255613 A1 | 10/2008 | Kaiser et al. |
| 2008/0312689 A1 | 12/2008 | Denham et al. |
| 2009/0036905 A1 | 2/2009 | Schmieding |
| 2009/0062846 A1 | 3/2009 | Ken |
| 2009/0062847 A1 | 3/2009 | Ken |
| 2009/0069823 A1 | 3/2009 | Foerster et al. |
| 2009/0082805 A1 | 3/2009 | Kaiser et al. |
| 2009/0240335 A1 | 9/2009 | Arcenio et al. |
| 2009/0248068 A1 | 10/2009 | Lombardo et al. |
| 2009/0259260 A1 | 10/2009 | Bentley et al. |
| 2009/0306711 A1 | 12/2009 | Stone et al. |
| 2009/0312776 A1 | 12/2009 | Kaiser et al. |
| 2009/0318961 A1 | 12/2009 | Stone et al. |
| 2010/0023056 A1 | 1/2010 | Johansson et al. |
| 2010/0114163 A1 | 5/2010 | Martin |
| 2010/0130989 A1 | 5/2010 | Bourque et al. |
| 2010/0145384 A1 | 6/2010 | Stone et al. |
| 2010/0211075 A1 | 8/2010 | Stone |
| 2010/0249809 A1 | 9/2010 | Singhatat et al. |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2011/0009867 A1 | 1/2011 | Oren et al. |
| 2011/0022061 A1 | 1/2011 | Orphanos et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0098728 A1 | 4/2011 | McDevitt et al. |
| 2011/0152885 A1 | 6/2011 | McDevitt et al. |
| 2011/0152929 A1 | 6/2011 | McDevitt et al. |
| 2011/0238111 A1 | 9/2011 | Frank |
| 2011/0264141 A1 | 10/2011 | Denham et al. |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0116450 A1 | 5/2012 | McDevitt et al. |
| 2012/0130422 A1 | 5/2012 | Hootstein |
| 2012/0150297 A1 | 6/2012 | Denham et al. |
| 2012/0197271 A1 | 8/2012 | Astorino et al. |
| 2012/0215257 A1 | 8/2012 | McDevitt et al. |
| 2012/0239085 A1 | 9/2012 | Schlotterback et al. |
| 2012/0290004 A1 | 11/2012 | Lombardo et al. |
| 2013/0018416 A1 | 1/2013 | Lombardo et al. |
| 2013/0023930 A1 | 1/2013 | Stone et al. |
| 2013/0035722 A1 | 2/2013 | McDevitt et al. |
| 2013/0110165 A1 | 5/2013 | Burkhart et al. |
| 2013/0123810 A1 | 5/2013 | Brown et al. |
| 2013/0123813 A1 | 5/2013 | Stone et al. |
| 2013/0138123 A1 | 5/2013 | Stone et al. |

(56) References Cited

U.S. PATENT DOCUMENTS

| | | |
|---|---|---|
| 2013/0158601 A1 | 6/2013 | Stone et al. |
| 2013/0237997 A1 | 9/2013 | Arai et al. |
| 2013/0296934 A1 | 11/2013 | Sengun |
| 2014/0114330 A1 | 4/2014 | Karasic et al. |

FOREIGN PATENT DOCUMENTS

| | | |
|---|---|---|
| EP | 2277456 A1 | 1/2011 |
| FR | 2743294 A1 | 7/1997 |
| GB | 2370227 A | 6/2002 |
| JP | H08052155 | 2/1996 |
| JP | 2006-503655 A | 2/2006 |
| JP | 2010-500912 A | 1/2010 |
| JP | 2010537746 | 12/2010 |
| JP | 2011-025036 A | 2/2011 |
| WO | 2003092551 A1 | 11/2003 |
| WO | 2004037094 A2 | 5/2004 |
| WO | 2006086275 A2 | 8/2006 |
| WO | 2007005394 A1 | 1/2007 |
| WO | 2007/037326 A1 | 4/2007 |
| WO | 2008/022250 A2 | 2/2008 |
| WO | 2009029914 A1 | 3/2009 |
| WO | 2012048050 A1 | 4/2012 |
| WO | 2012103536 A1 | 8/2012 |
| WO | 2012112793 A1 | 8/2012 |
| WO | 2013134277 A1 | 9/2013 |
| WO | 2014062684 A1 | 4/2014 |

OTHER PUBLICATIONS

Office Action from related European Application No. 13712402.0-1654 dated Nov. 4, 2016.
Office Communication from related European Application No. 13786021.9-1654 dated Dec. 13, 2016.
U.S. Appl. No. 61/443,325, filed Feb. 16, 2011, McDevitt et al.
U.S. Appl. No. 61/422,859, filed Dec. 14, 2010, McDevitt et al.
U.S. Appl. No. 61/419,334, filed Dec. 3, 2010, McDevitt et al.
U.S. Appl. No. 61/410,027, filed Nov. 4, 2010, McDevitt et al.
U.S. Appl. No. 61/328,251, filed Apr. 27, 2010, Overes.
U.S. Appl. No. 61/398,699, filed Jun. 29, 2010, Overes et al.
U.S. Appl. No. 61/432,755, filed Jan. 14, 2011, Henrichsen et al.
U.S. Appl. No. 61/461,490, filed Jan. 18, 2011, Henrichsen et al.
U.S. Appl. No. 61/443,142, filed Feb. 15, 2011, Overes.
U.S. Appl. No. 61/517,230, filed Apr. 15, 2011, Lombardo.
U.S. Appl. No. 61/517,221, filed Apr. 15, 2011, Lombardo et al.
U.S. Appl. No. 61/517,203, filed Apr. 15, 2011, Lombardo et al.
U.S. Appl. No. 61/518,519, filed May 6, 2011, Lombardo et al.
U.S. Appl. No. 61/538,163, filed Sep. 23, 2011, Burkhart et al.
U.S. Appl. No. 61/559,672, filed Nov. 14, 2011, Brown et al.
"Technique for ACL reconstruction with Acufex Director Drill Guide and Endobutton CL" copyright 1999, Smith & Nephew, Inc., 20 pages.
"Endobutton Direct: Fixation Device," Smith & Nephew, Inc., reprinted from http://global.smith-nephew.com/us/product23376_5895.htm, on Nov. 22, 2010, 3 pages.
"Endobutton CL," Smith and Nephew, Inc., reprinted from http://endo.smith-nephew.com/es/Standard.asp?NodeID=2715, on Nov. 22, 2010, 1 page.
From, Stuart, "ACL Reconstruction with Bone-Tendon-Bone Transplants using the Endobutton CL BTB Fixation System," Smith & Nephew, Inc., copyright 2004, printed on Apr. 4, 11 pages.
Scope This Out, vol. 10, No. 2, Summer 2008, 8 pages.
Scope This Out, vol. 12, No. 2, Fall 2010, 8 pages.
Scope this Out, vol. 12, No. 1, Spring 2010, 8 pages.
ToggleLOC: Femoral Fixation Device with Zip Loop Technology, Biomet Sports Medicine, Inc., 2007, 8 pages.
Glousman, R., et al., "JuggerKnot Soft Anchor Surgical Technique," Biomet Sports Medicine, 2010, 1 page.
Game Plan: Innovative Products to be Launched AAOS 2010, Biomet Sports Medicine, Spring 2010, vol. 2, No. 3, 1 page.
Lawhorn, K., "MaxFire MarXmen Device Surgical Technique," Biomet Sports Medicine, 2010, 1 page.
International Search Report for International Application No. PCT/US2012/023056, dated Jun. 13, 2012.
Shoulder Restoration System: Y-KnotTM 1.3mm All-Suture Anchor, ConMedTM Linvatec, 2011, 4 pages.
Shoulder Restoration System: Arthroscopic Bankart Repair Using the Y-KnotTM 1.3mm All-Suture Anchor, ConMedTM Linvatec, 2011, 4 pages.
International Search Report Application No. PCT/US2013/029143, dated Jun. 13, 2013.
International Search Report Application No. PCT/US2013/065064, dated Feb. 21, 2014.
Written Opinion of the International Searching Authority and the and International Preliminary Report on Patentability for International Application No. PCT/US2012/023056, dated Jun. 13, 2012.
Office Action from related Chinese Application No. 201380066543.7 dated Sep. 27, 2016.
Office Action from related Japanese Application No. 2014-561043 dated Jan. 16, 2017.
First Office Action from related Chinese Application No. 201380013146.3 dated Apr. 14, 2016.
Translation of Search Report from related Chinese Application No. 201380013146.3 dated May 26, 2016.
Patent Examination Report from related Australian Application No. 2013230095 dated Nov. 2, 2016.
Decision of Rejection from related Japanese Application No. 2013-551405 dated Jul. 25, 2016.
International Search Report from corresponding International Application No. 201380066543.7, dated Dec. 29, 2017.

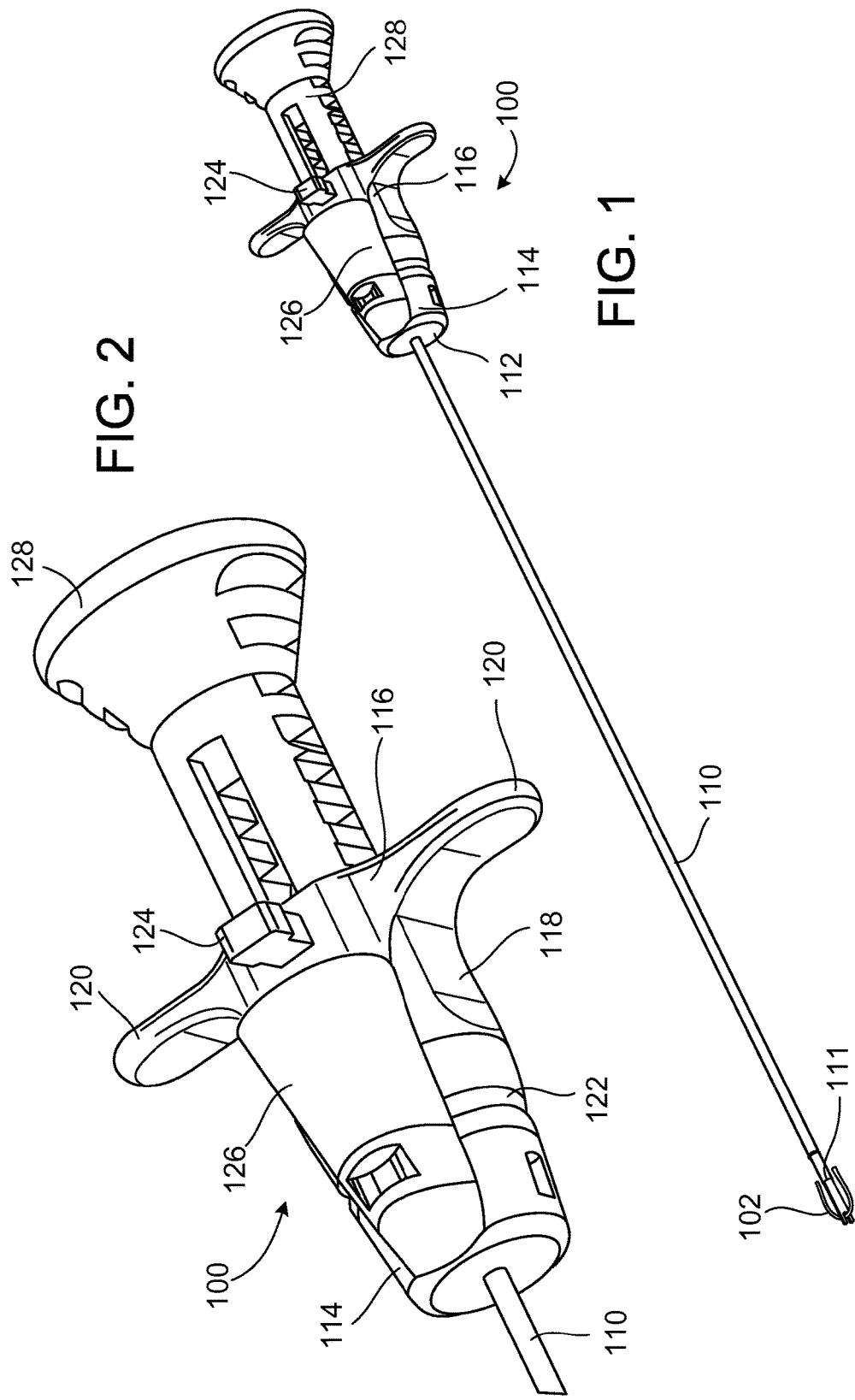

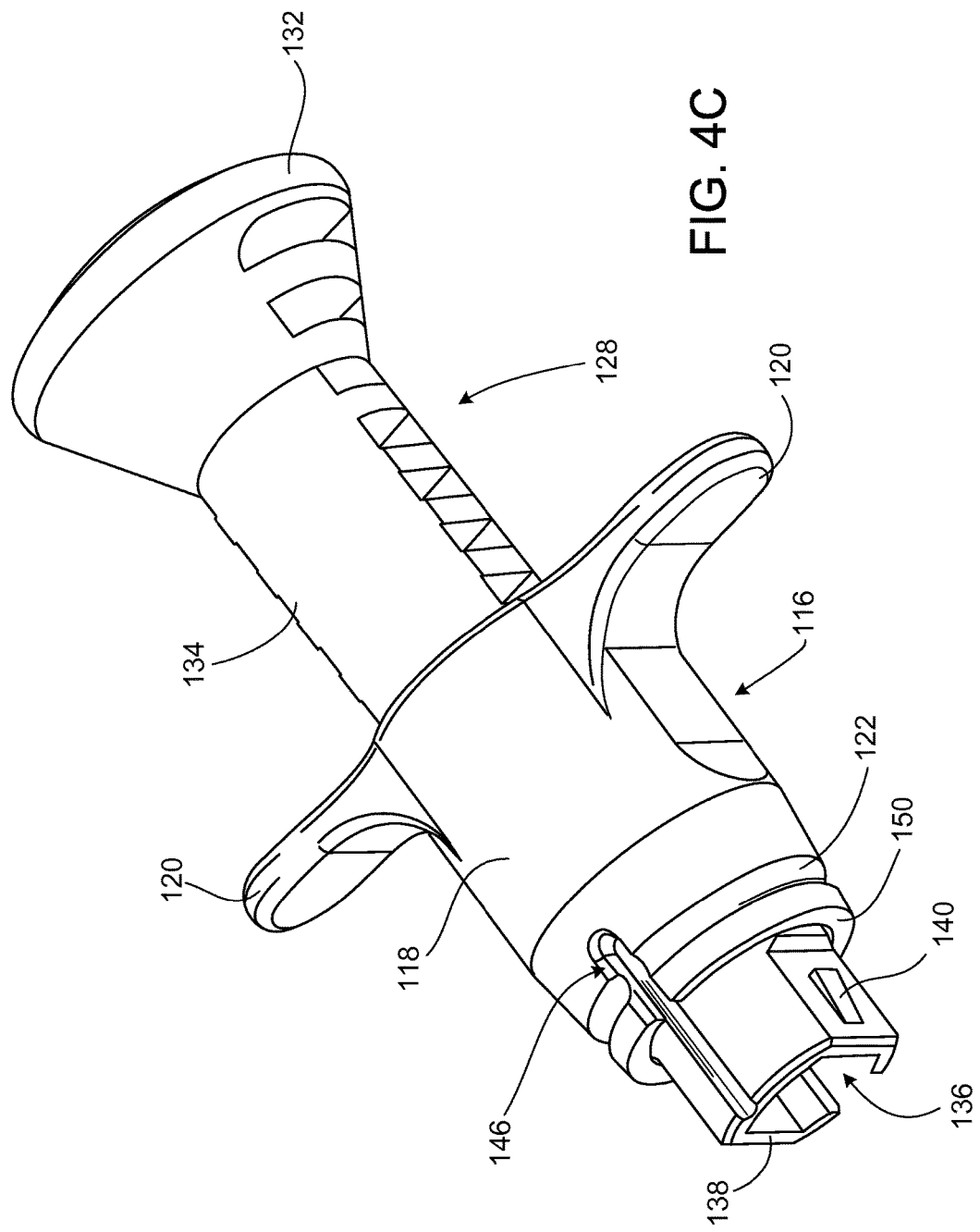

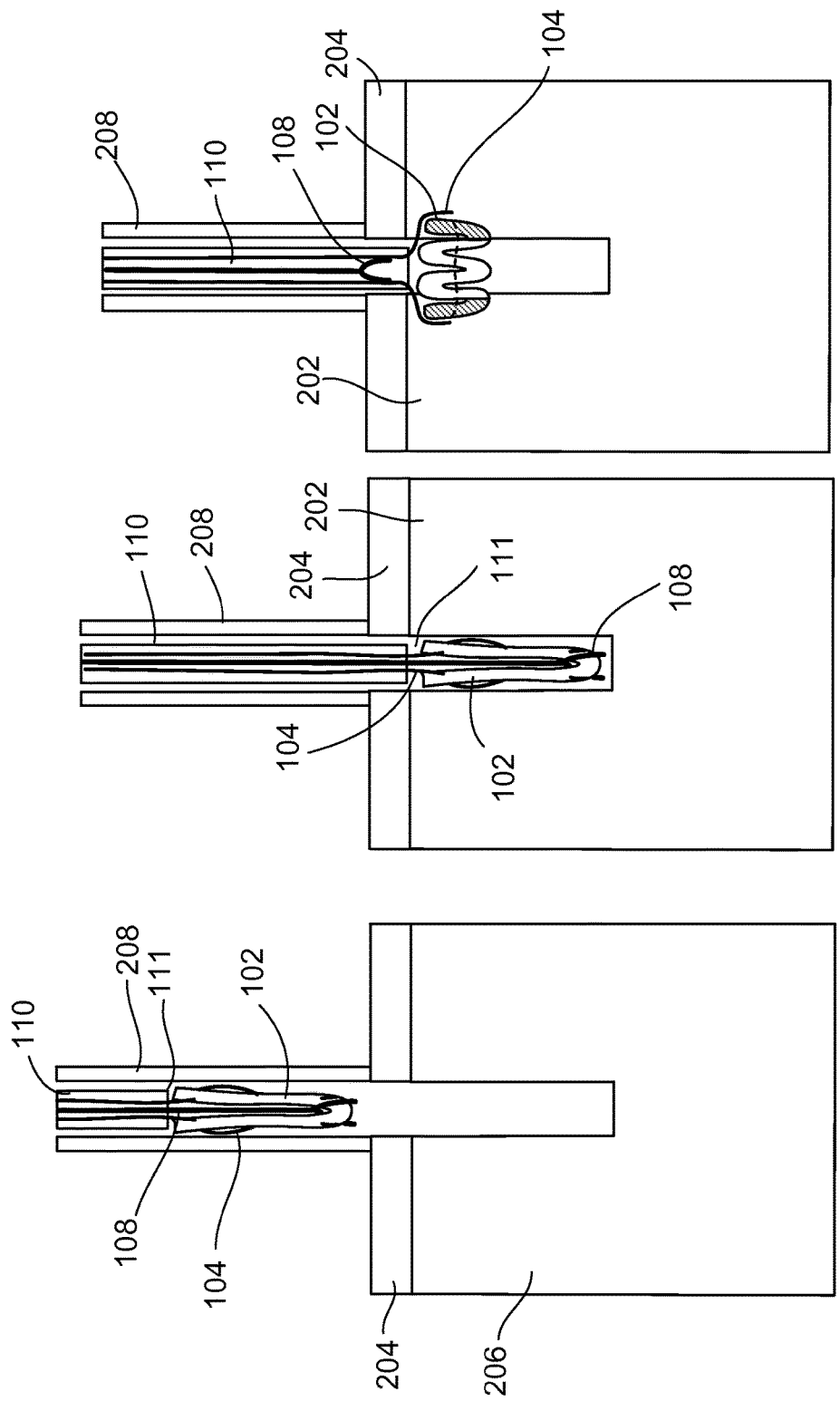

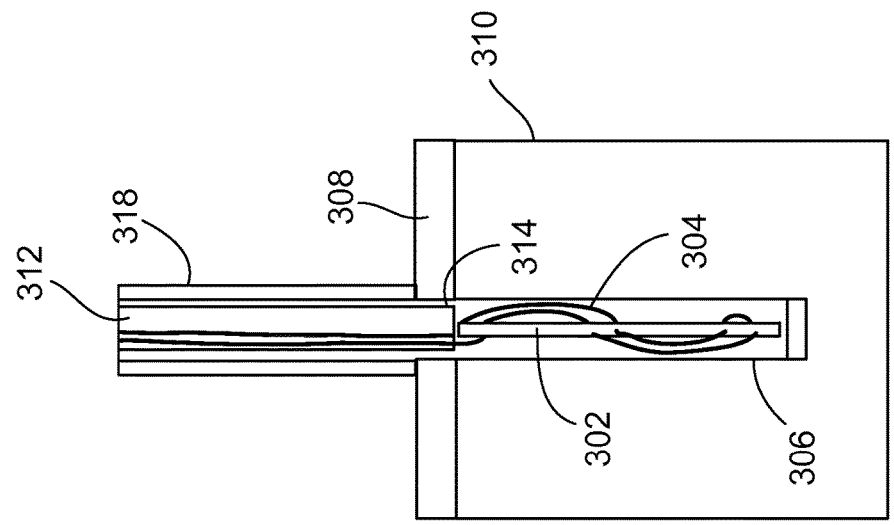
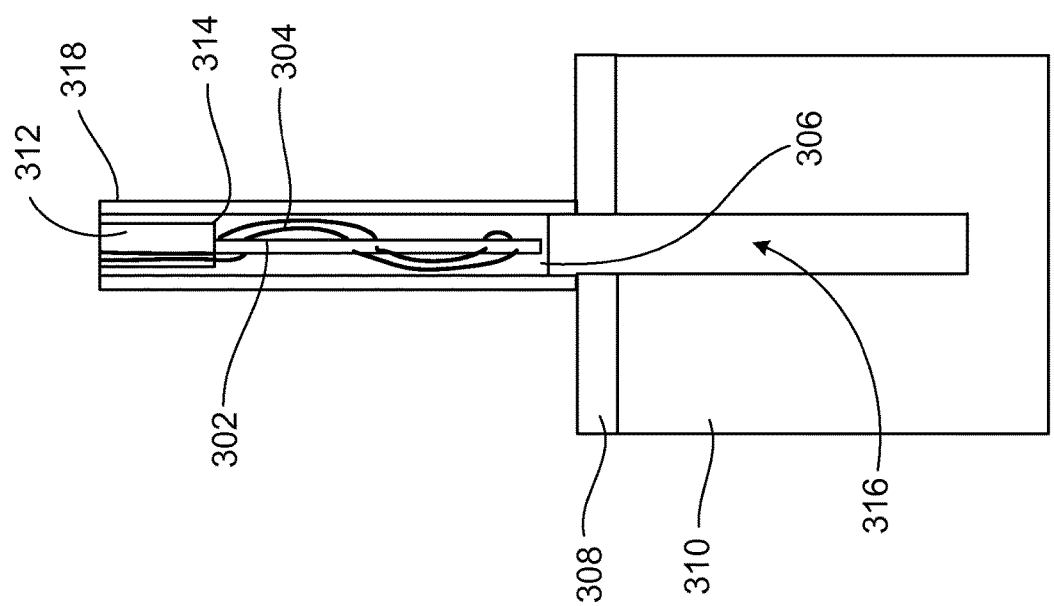
FIG. 13C
FIG. 13B

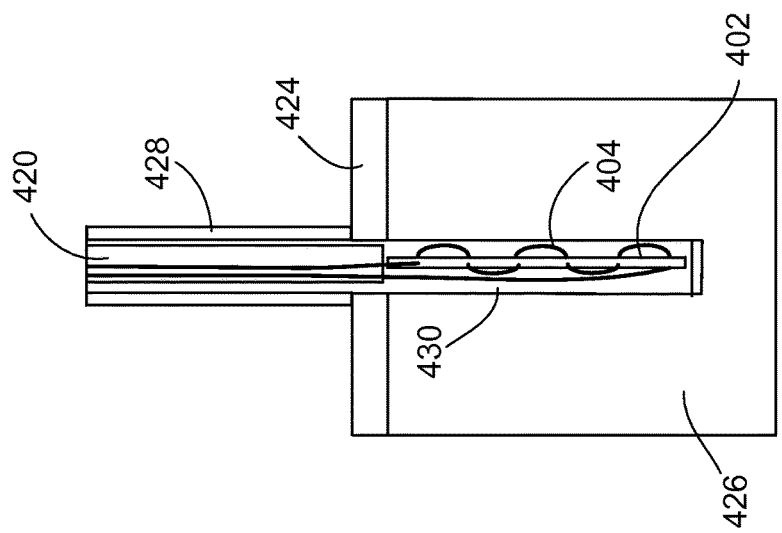
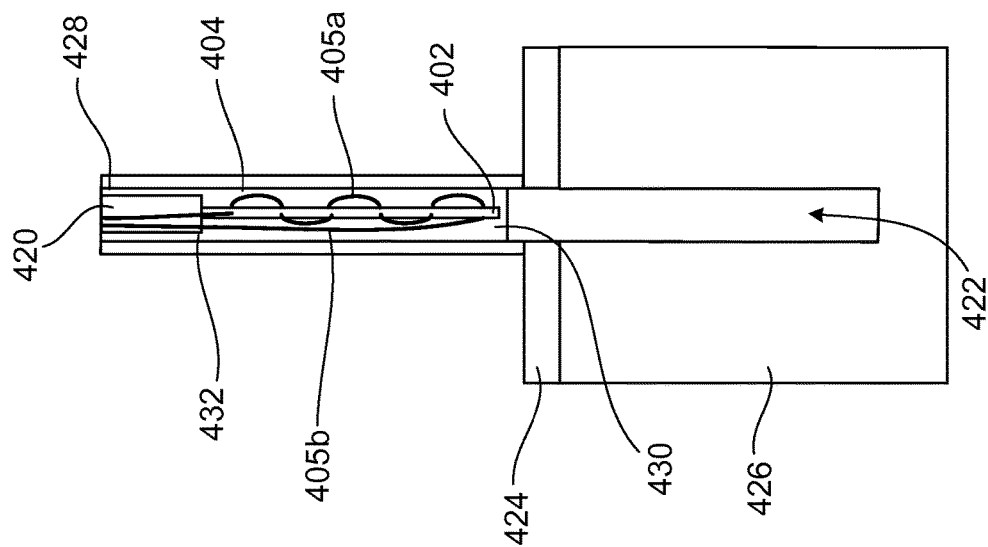
FIG. 14A
FIG. 14B

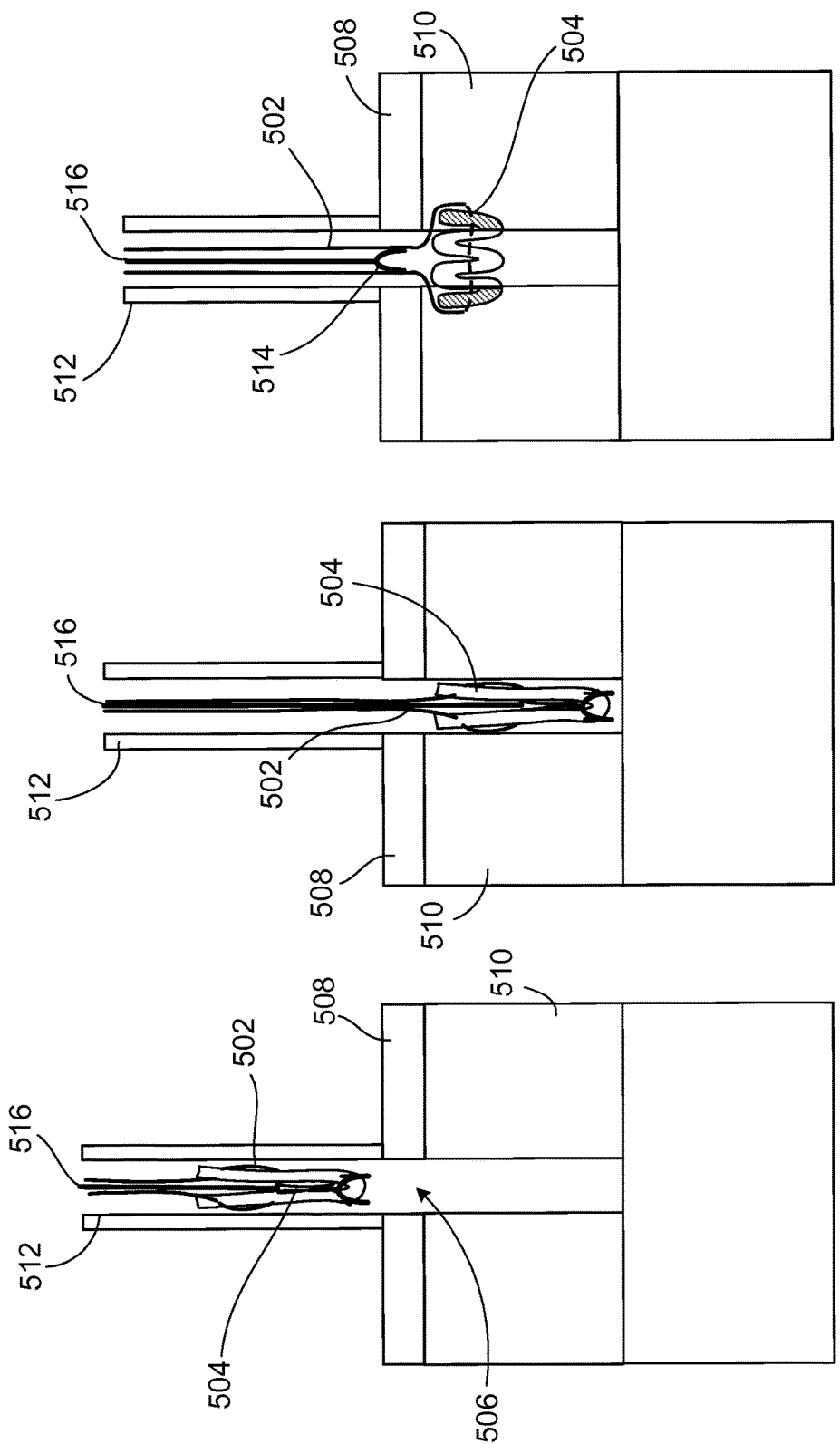

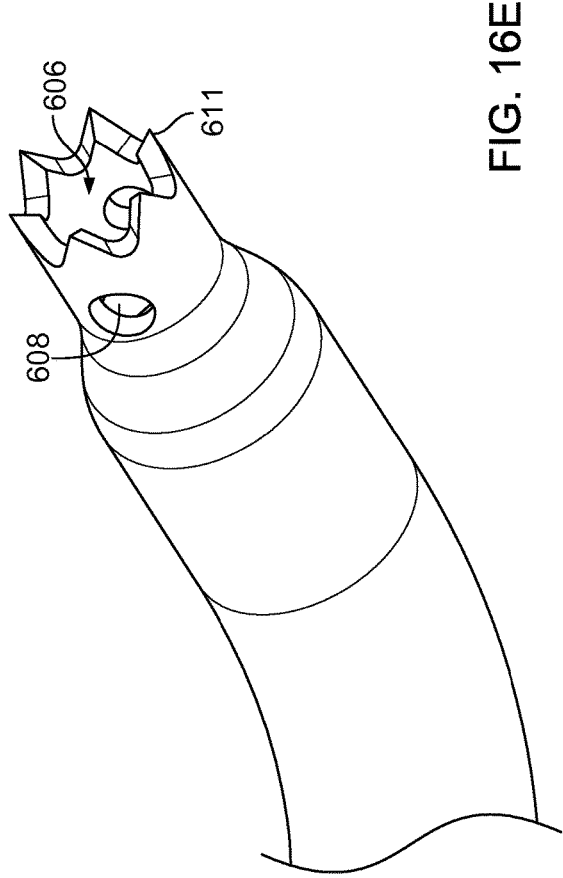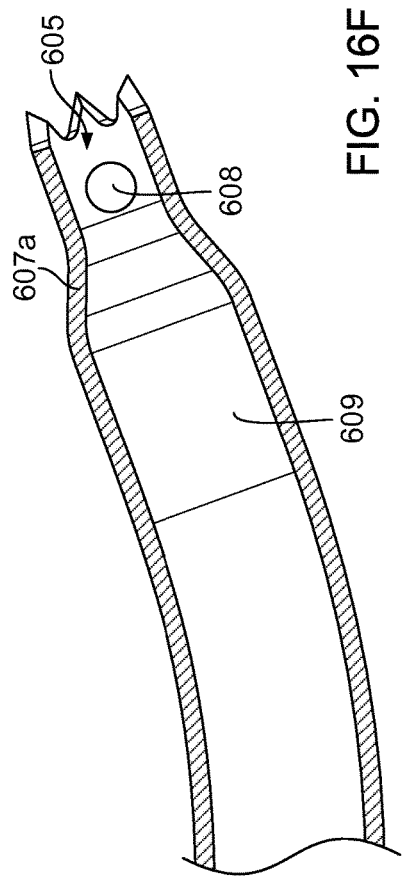
FIG. 16E
FIG. 16F

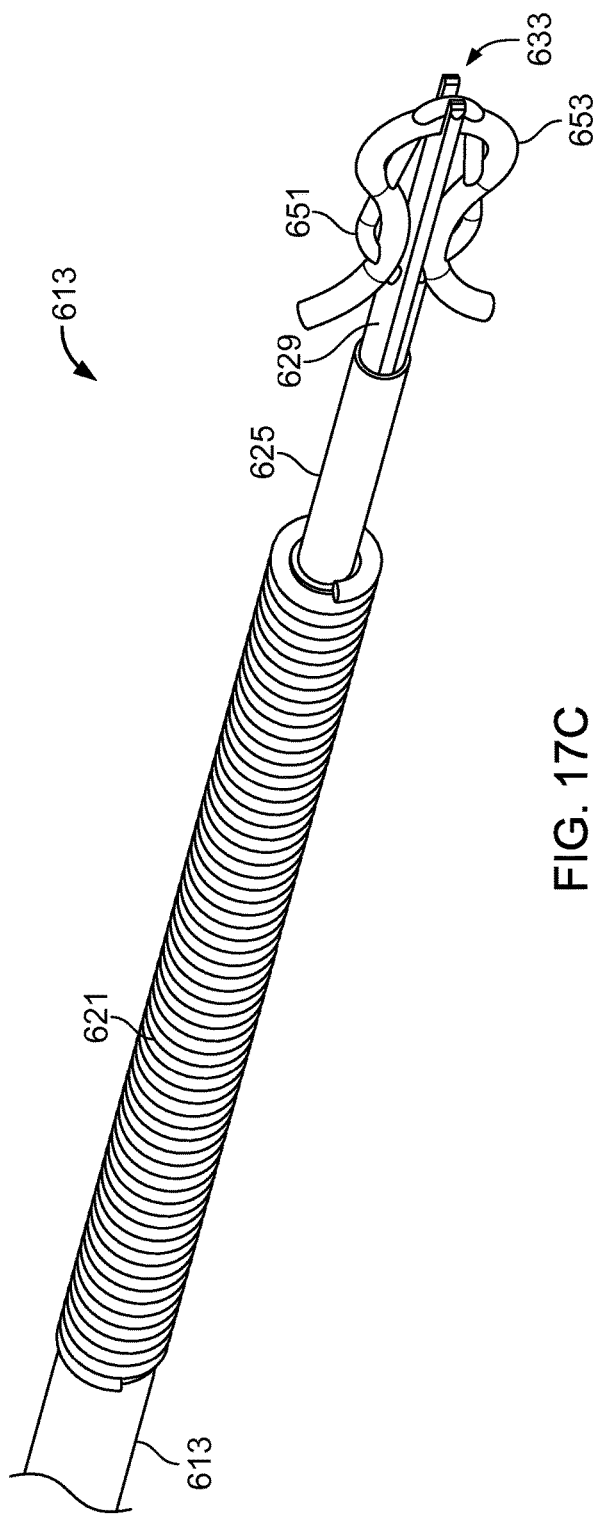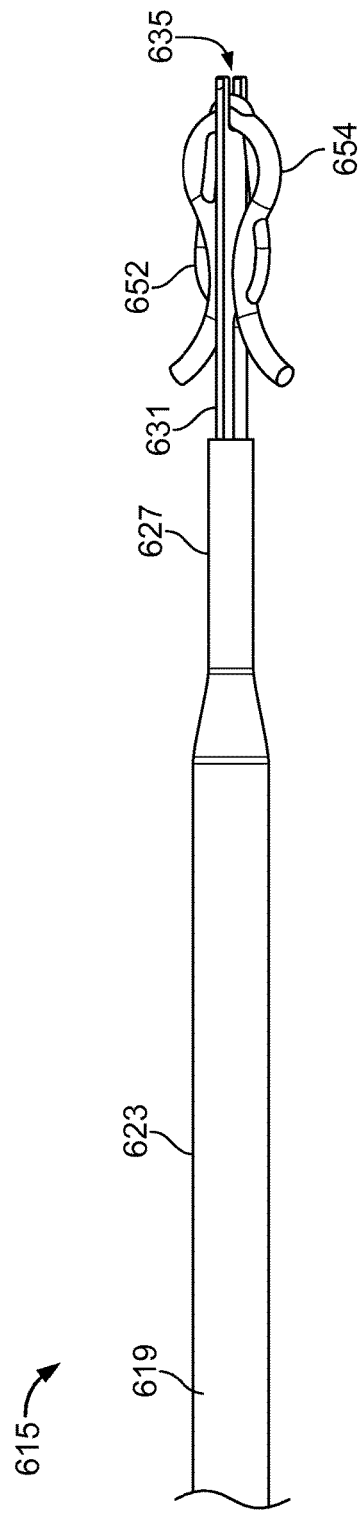
FIG. 17C
FIG. 17D

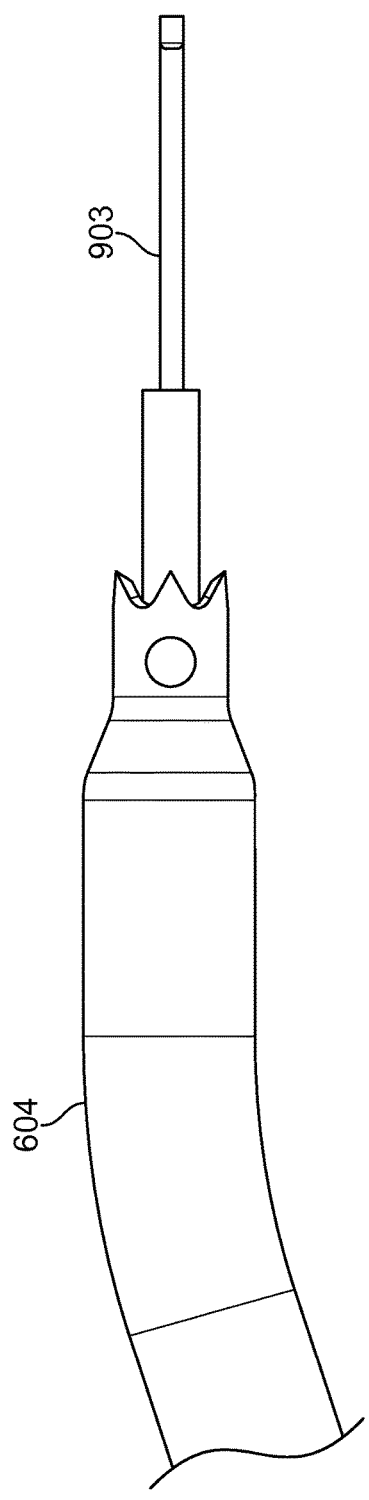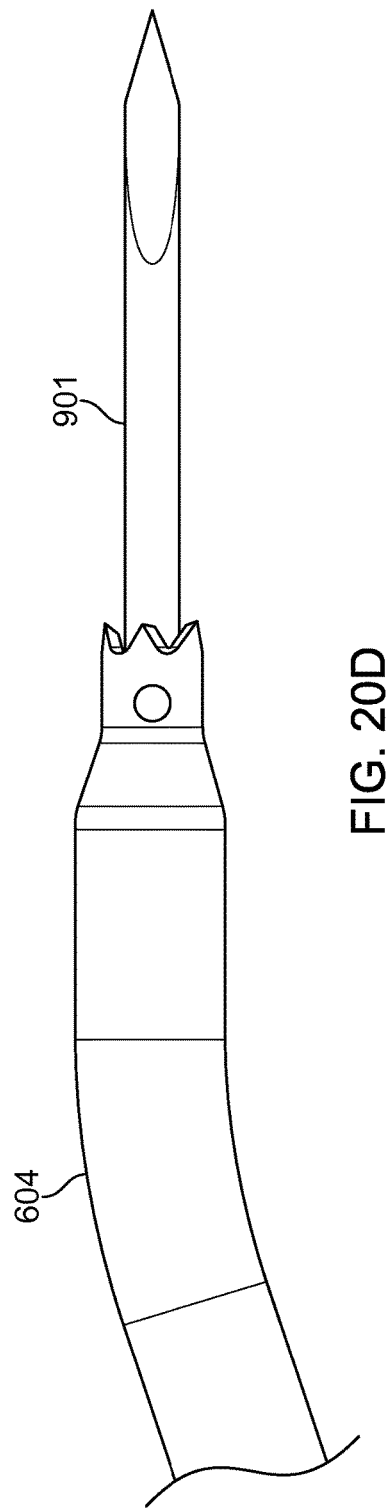
FIG. 20C
FIG. 20D

FLEXIBLE ANCHOR DELIVERY SYSTEM

CROSS-REFERENCE TO RELATED APPLICATION(S)

This application is a continuation of U.S. application Ser. No. 13/654,855, filed Oct. 18, 2012, entitled "FLEXIBLE ANCHOR DELIVERY SYSTEM," the entirety of which is incorporated herein by reference.

TECHNICAL FIELD

This disclosure relates to apparatus and methods for repairing tissue.

BACKGROUND

Arthroscopic procedures using sutures and suture anchors have been used in tissue repair to, for example, secure soft tissue to bone. These anchors may not fully deploy below the cortical layer. An anchor that is not fully deployed at the time of installation does not provide maximum fixation and could migrate later causing the repair suture to loosen, sacrificing the integrity of the repair. An anchor not providing its maximum fixation may result in pull out during or after the repair procedure. Anchors may also be damaged during insertion. Fraying of the anchor and repair sutures, or other damage, may result in a number of problems including compromised anchor construct, anchor severing, repair suture severing, the repair suture pulling through the anchor, etc.

SUMMARY

The details of one or more implementations of the disclosure are set forth in the accompanying drawings and the description below. Other features and advantages will be apparent from the description and drawings, and from the claims.

In one aspect, an assembly includes a flexible fixation member, a suture, and a delivery device. The flexible fixation member includes a body with two terminal ends. A suture passes through the flexible fixation member at various points along a length of the body between the terminal ends such that portions of the fixation member are slidable relative to the suture and configurable to form a cluster within a surgical site. The delivery device includes a tubular member, an elongated inserter, and a trigger. The elongated inserter is slidably disposed within the tubular member. The inserter has a forked distal end and a proximal end, the forked distal end is configured to receive a portion of the flexible fixation member and the suture. The trigger is finger-engagable and is fixedly coupled to the proximal end of the inserter. It is configured to advance and retract the inserter relative to the tubular member. The trigger includes a retention member for retaining a proximal end portion of the suture.

Implementations may include one or more of the following. For example, the delivery device may further include a handle to which the trigger is slidably coupled. The delivery device may further include a button coupled to the trigger and the handle and configured to permit the trigger to slide relative to the handle when the button is depressed. The handle may define a plurality of cutout portions along a length of the handle. The cutout portions are configured to receive a portion of the button therein to fixedly engage the trigger to the handle. The trigger may further include a circumferential groove defined about a periphery of the trigger. A length of the suture may be wrapped about trigger at least once and retained in the groove. The trigger may define a slot configured to receive a portion of the suture therethrough and direct the suture into the groove. The trigger may have a substantially cylindrical body and a pair of finger-engagable elements extending laterally from the body. The delivery device may also include a cover disposed over the retention member. The handle may define two openings in a distal end of the handle such that the suture passes from an interior to an exterior of the handle through the first of the two openings and the suture passes from the exterior to the interior of the handle through the second of the two openings. The delivery device may further include a cover element releasably coupled to a distal end of the handle and fixed coupled to a proximal end of the tubular member. The suture may pass through the fixation member to form two substantially parallel tail sections of suture. The fixation member may be non-tubular. The flexible fixation member and the suture may comprise a size 2 suture.

In another aspect, a method of closing a tissue wound, includes delivering a wound closure assembly to a surgical site, advancing an inserter distally relative to a tubular member to position the flexible fixation member within a targeted tissue site, tensioning a suture to form a cluster of the portions of the fixation member within the surgical site, and retracting the inserter proximally relative to the tubular member to remove the forked distal end of the inserter from within the targeted tissue site. The wound closure assembly including a flexible fixation member, a suture, and a delivery device. The flexible fixation member includes a body having two terminal ends. The suture passes through the flexible fixation member at various points along a length of the body between the terminal ends such that portions of the fixation member are slidable relative to the suture and configurable to form a cluster within a surgical site. The delivery device has a tubular member, an elongated inserter slidably disposed within the tubular member, and a finger-engagable trigger. The inserter has a forked distal end, configured to receive a portion of the flexible fixation member and the suture therein. The finger-engagable trigger is fixedly coupled to the proximal end of the inserter and configured to advance and retract the inserter relative to the tubular member. The trigger comprises a retention member for retaining a proximal end portion of the suture.

Implementations may include one or more of the following. For example, tensioning the suture to form the cluster of the portions of the fixation member with the surgical site may include pulling the fixation member against a distal end of the tubular member. Tensioning the suture may be carried out by moving the trigger in a proximal direction relative to the tubular member. Retracting the inserter may be carried out by moving the trigger in a proximal direction relative to the tubular member. Tensioning the suture and retracting the inserter are carried out by moving the trigger in a proximal direction relative to the tubular member such that the forked end of the inserter is moved proximally over a distance before tensioning of the suture begins. The method may further include drilling a hole into the tissue.

BRIEF DESCRIPTION OF THE DRAWINGS

FIG. 1 is a perspective view of a delivery device.

FIG. 2 is a perspective view of a proximal portion of the delivery device of FIG. 1.

FIGS. 4B-4D are perspective views of a partial assembly of the proximal portion of the delivery device of FIG. 1 including the trigger of FIG. 4A.

FIGS. 12A-12C illustrate the method of use of the distal end of a delivery device with the flexible fixation member and suture assembly of FIG. 10.

FIGS. 13B-13E illustrate the method of use of the distal end of a delivery device with the flexible fixation member and suture assembly of FIG. 13a.

FIGS. 14A-14D illustrate the method of use of time distal end of a delivery device with another flexible fixation member and suture assembly.

FIGS. 15A-15C illustrate the method of use of the distal end of a delivery device with another flexible fixation member and suture assembly FIGS. 16A-16F are perspective views of an angled guide.

FIGS. 17A-17E are perspective views of a flexible delivery device.

FIG. 20C is a perspective view the distal end of an angled swaged guide and flexible inserter.

FIG. 20D is a perspective view of the distal end of an angled guide and flexible drill.

DETAILED DESCRIPTION

Figure 8:
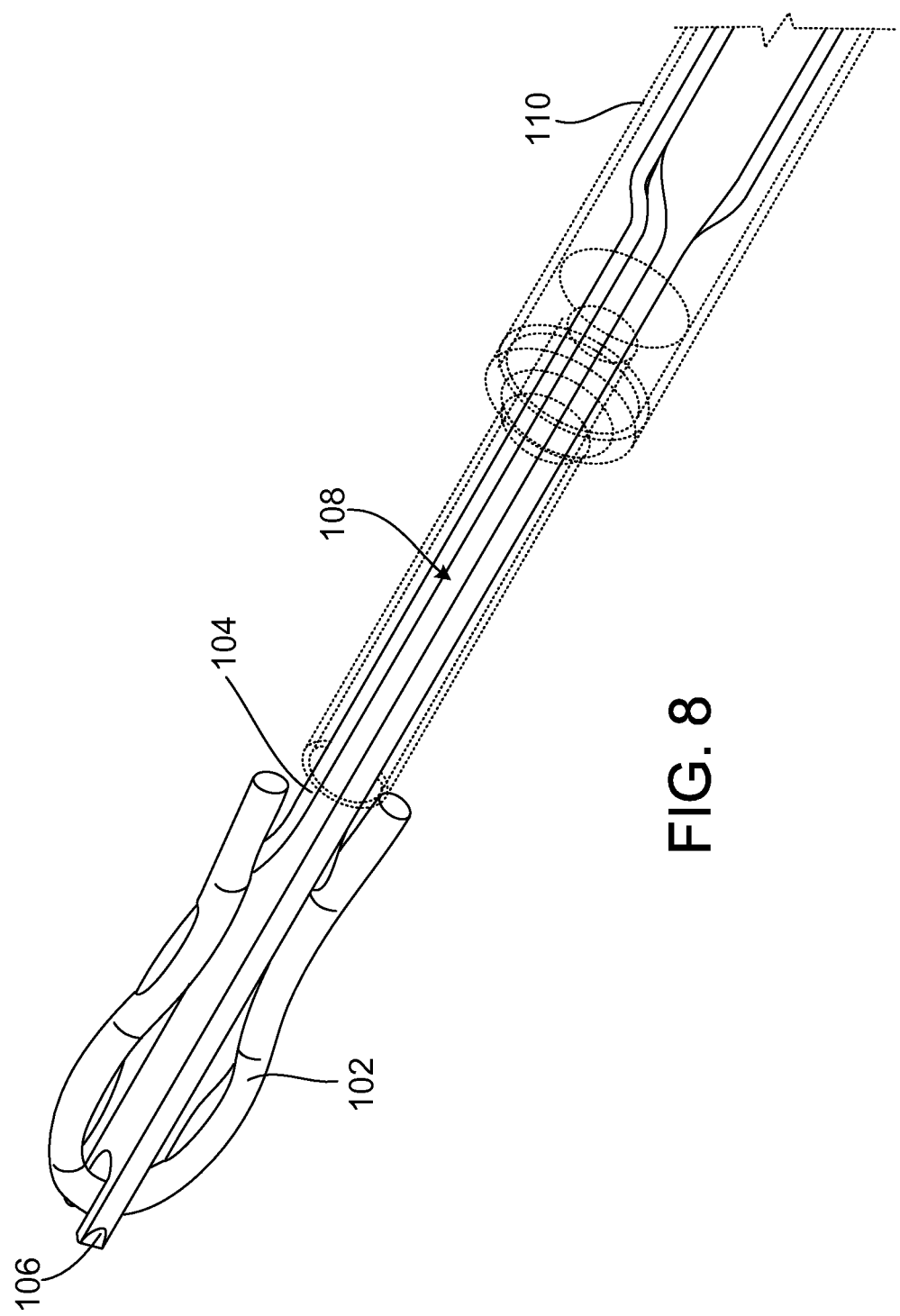

FIG. 1 shows a surgical device 100 used for delivering one or more fixation members to a surgical site. The device 100 includes a handle 128, a trigger 116 movable coupled to the handle 128, a cover element 114 coupled to the trigger 116, a tubular member 110 attached to the cover element 114, and fixation member or anchor 102 having a flexible member or suture 104 (FIG. 8) interwoven through the fixation member 102. The fixation member 102 and suture 104 are disposed in a distal end 106 of an elongated inserter 108 (FIG. 8). The elongated inserter 108 is slidably positioned within the tubular member 110. The proximal end 112 of tubular member 110 is coupled to the cover element 114. The proximal end of the delivery device 100 is shown in more detail in FIG. 2. The cover element 114 is coupled to a cover 126 and the trigger 116. The trigger 116 includes a body 118, finger engagable elements 120 emending generally perpendicular from a longitudinal axis of the body 118, a circumferential groove 122, and a button 124. The trigger 116 is movably coupled to the handle 128. The button 124 interacts with cutout portions 130 (FIG. 3) in the handle 128 to lock the motion of the trigger 116 with respect to the handle 128. The button 124 can be depressed, which eliminates the interference between the button 124 and the cutouts 130 allowing motion of the trigger 116 with respect to the handle 128.

Figure 3A:
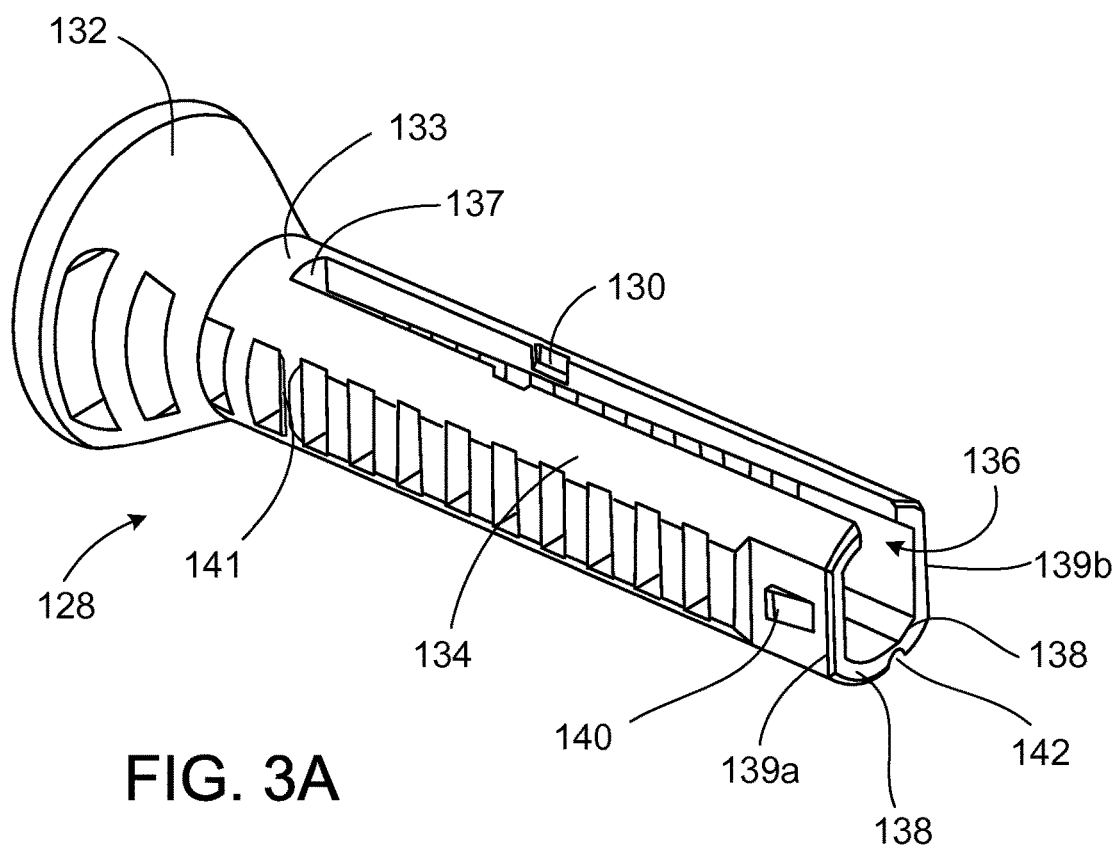
FIGS. 3A and 3B are perspective views of a handle of the delivery device of FIG. 1.
Figure 3B:
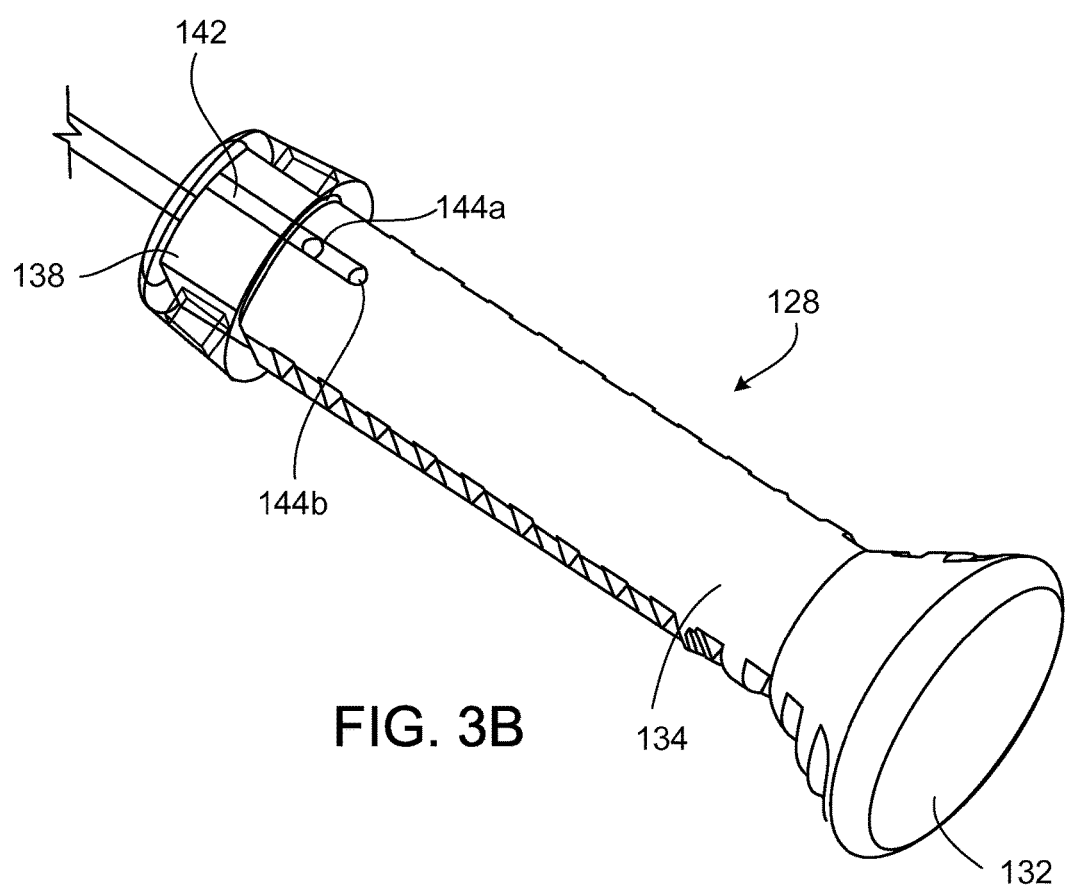

Referring to FIGS. 3A and 3B, the handle 128 includes an enlarged proximal end 132 that may enhance a user's grip on the handle 128. The proximal end 132 is connected to or formed integral with a hollow elongated body 134. The body 134 includes a longitudinal slot 136 extending from a distal end 138 at least partially toward the proximal end 132. One of the enlarged proximal end 132 or the proximal wall 137 of the slot 136 may act as a stop for the trigger 116. Distal end 138 also includes two straight portions 139a and 139b. Cut out portions 130 are provided along the slot 136 and are sized to receive a portion of the button 124. The distal end 138 includes mating features 140 to couple with the cover element 114. The proximal end 133 of the body 134 includes a protrusion 141 which interacts with the trigger 116 to act as a detent for the trigger 116 in the deployed orientation. The interaction of protrusions 141 and the trigger 116 may also create an audible click or sound. Groove 142 and openings 144a, 144b in the distal end 138 of the handle 128 allow for routing of the suture 104 as will be explained in more detail below.

Figure 4A:
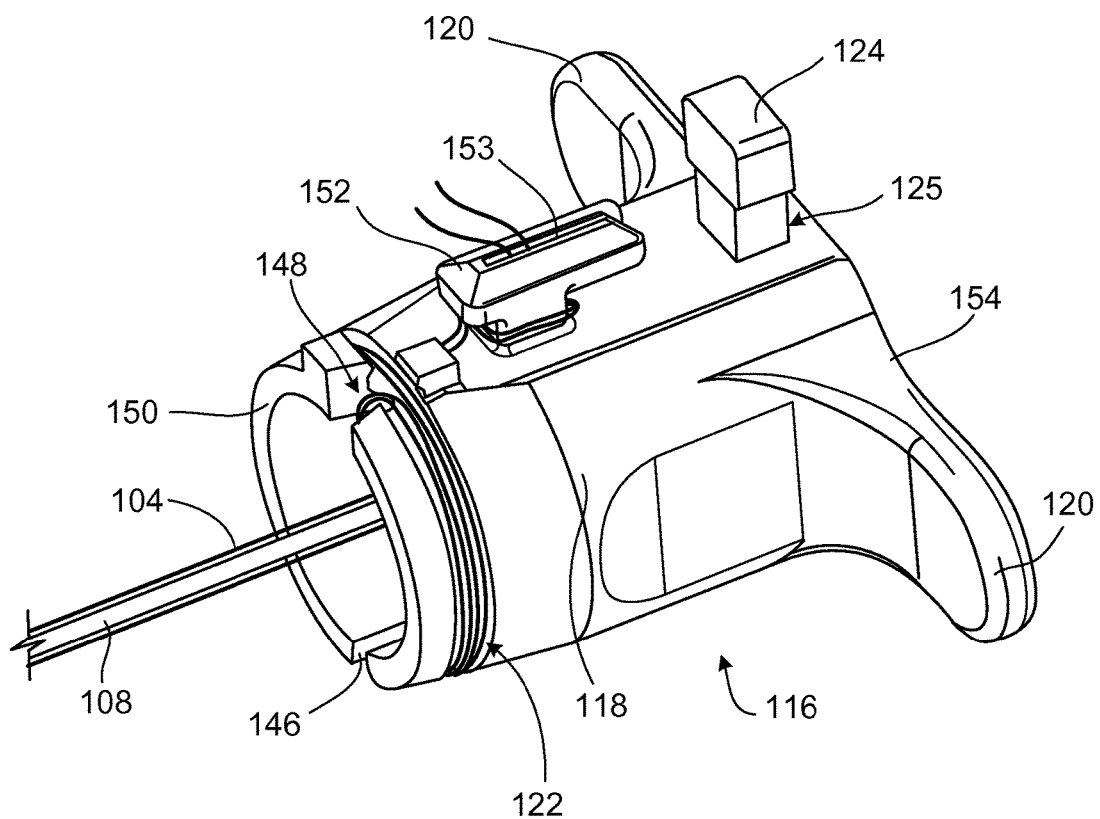
FIG. 4A is a perspective view of a trigger of the delivery device of FIG. 1.
Figure 4B:
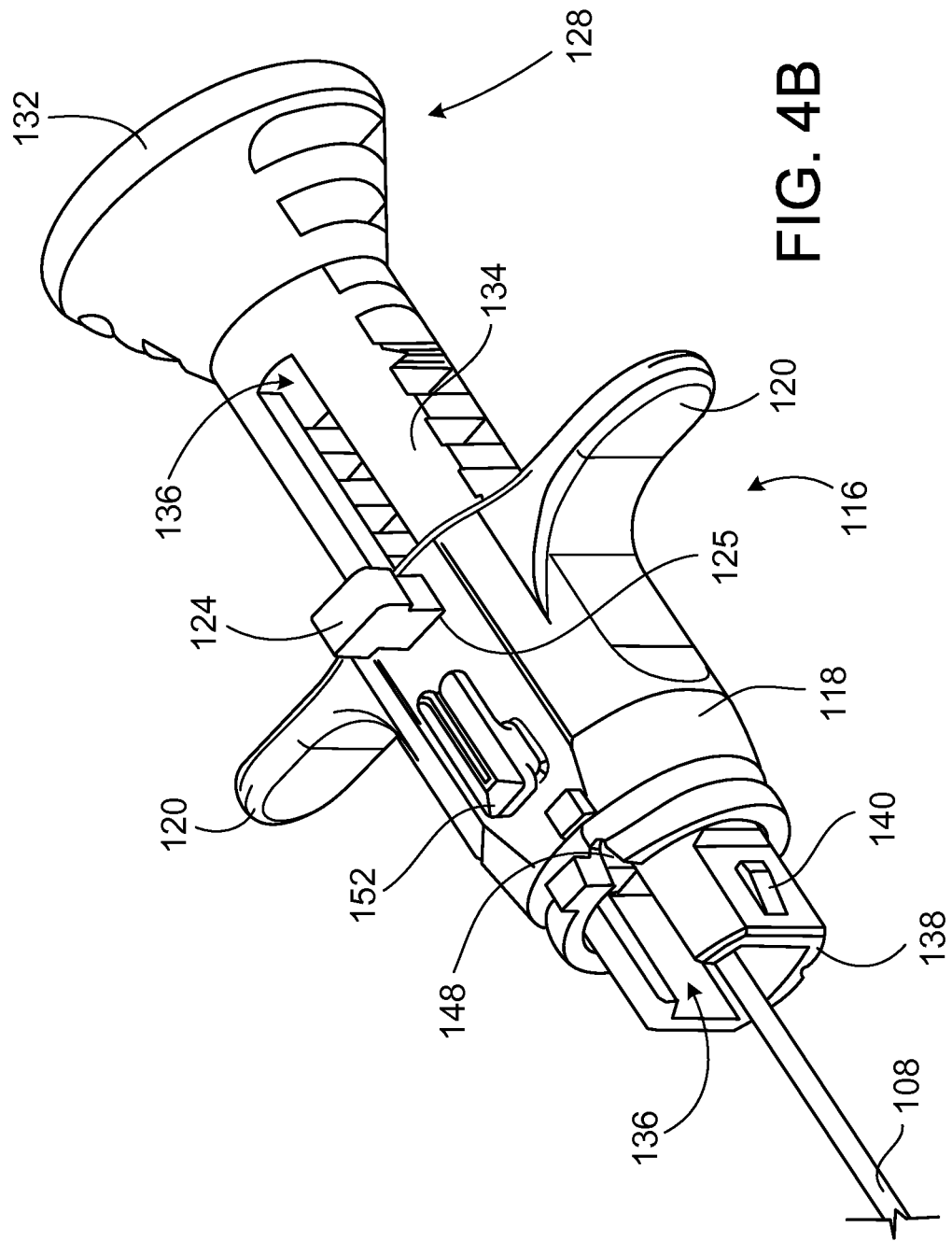

The trigger 116, shown in FIG. 4A, includes two finger engagable elements 120 protruding from either side of the body 118. The finger engagable elements 120 are designed to be grasped by a surgeon's fingers while the device is being operated, as described in more detail below. Slots 146 and 148 extend from the distal end 150 of the trigger 116 and may be in contact with the groove 122. The slot 148 and the groove 122 are designed for routing of the suture 104 as shown. The groove 122 runs circumferentially around the trigger's body 118 and allows for longer sutures to be wrapped around it, increasing the length of suture that can be used with the delivery device 100. Trigger 116 also includes a retention member 152 with a slot 153 which is used to cleat sutures 104 to keep them in place. Button 124 fits in a rectangular cutout 125 in the proximal end 154 of the trigger 116. In its upright position, the button 124 engages cutout portions 130 of the handle 128 (FIG. 3A) and prevents the trigger 116 from moving with respect to the handle 128. When the button 124 is depressed, the trigger 116 is free to slide up and down the body 134 of the handle 128.

FIGS. 4B-4E show the trigger 116, handle, 128, and elongated inserter 108 in an assembled configuration. The elongated inserter 108 is attached to a tongue 156 of the trigger 116 by, for example, insert molding, friction fit, welding or some other suitable attachment means, such that the elongated inserter 108 moves with the trigger 116. The proximal end of the elongated inserter 108 has reliefs 172 (FIG. 6) to prevent the inserter 108 from pushing through the tongue 156 in the trigger 116. The tongue 156 of the trigger 116 fits through the slot 136 and within the hollow portion of the body 134 of the handle 128, while the body 118 of the trigger 116 is slidingly coupled to the body 134 of the handle 128. The mating features 158 of the button 124 may engage the cutout portions 130 of the handle 128, when the button is in its upright position (FIG. 4E) to prevent the trigger 116 from moving with respect to the handle 128. The trigger 116 may be injection molded and made of ABS. The trigger 116 and the handle 128 are made of dissimilar materials to reduce the friction between the two which allows the trigger to slide along the body 134 of the handle more easily.

Figure 4D:
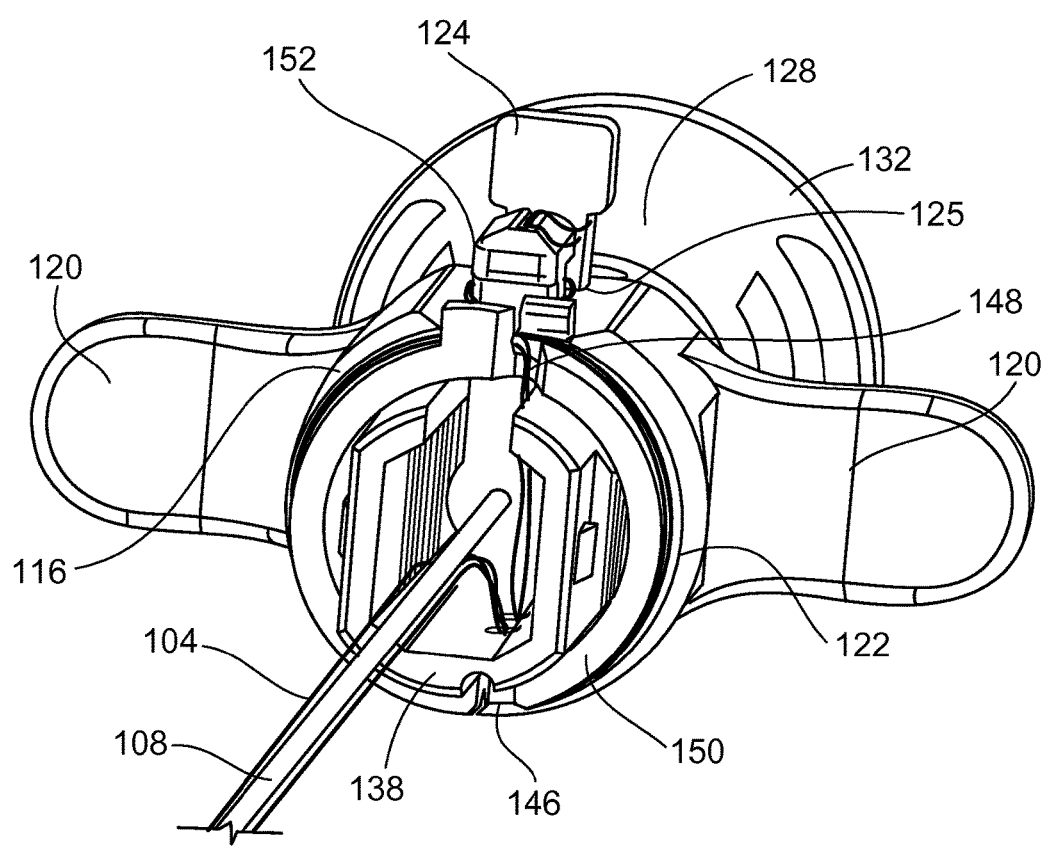
Figure 4E:
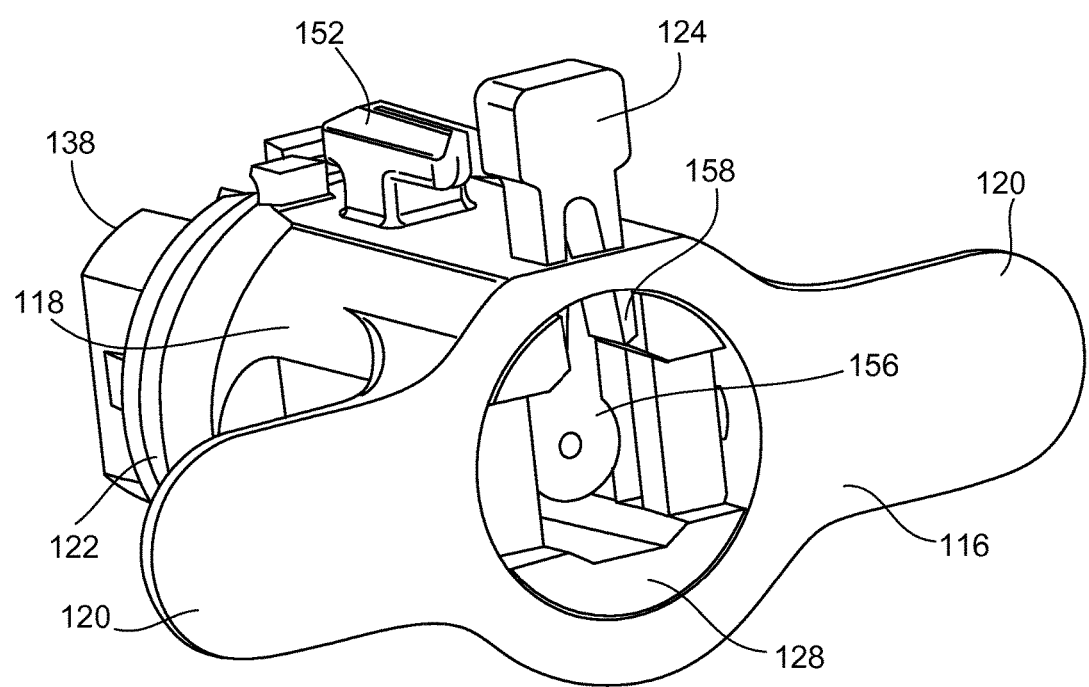
FIG. 4E is a cutaway view of a partial assembly of the proximal portion of the delivery device of FIG. 1.

As shown in FIGS. 4A and 4D, the suture 104 travels down the elongated inserter 108 and is routed out of the handle 128 through hole 144a, and then back through hole 144b before passing out of slot 148 and wrapping around trigger 116. Some slack is left in the suture 104. The ends of the suture 104 can be secured in the slot 153 on the retention member 152.

Figure 5A:
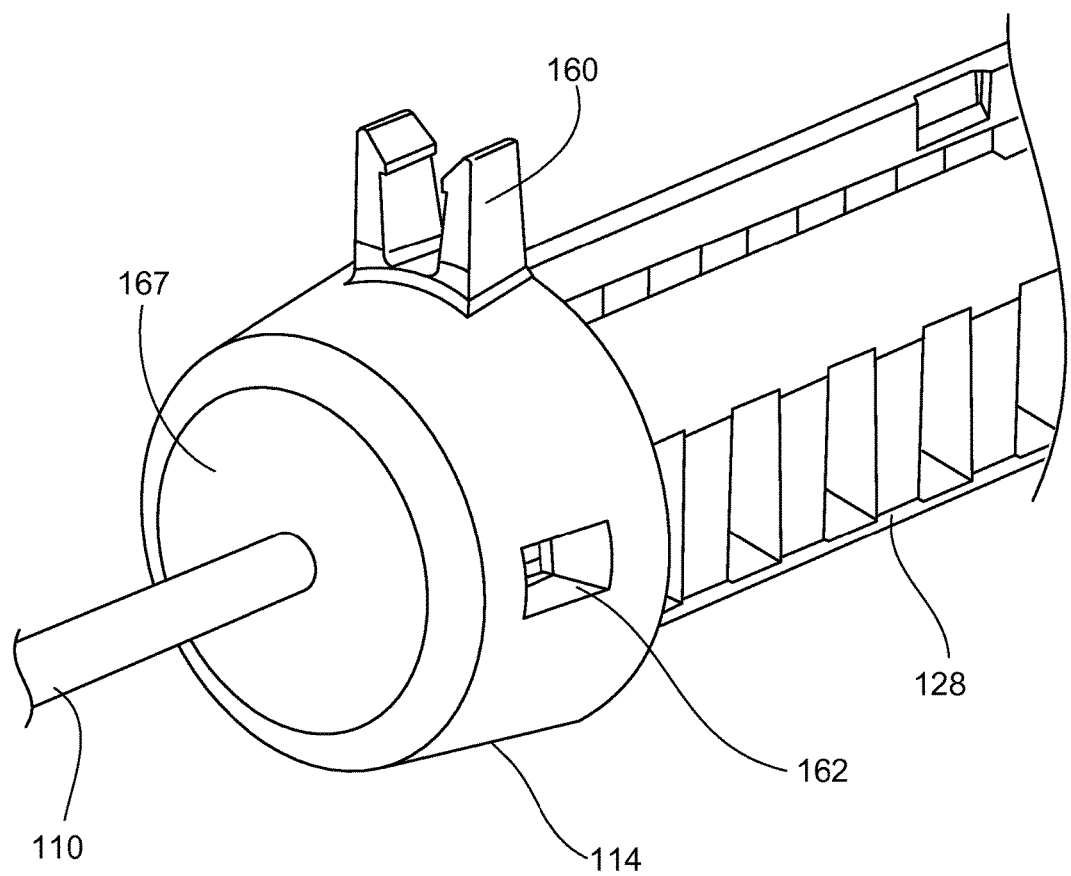
FIGS. 5A and 5B are perspective views of a partial assembly of the proximal portion of the delivery device of FIG. 1 including a cover element and tubular member.
Figure 5B:
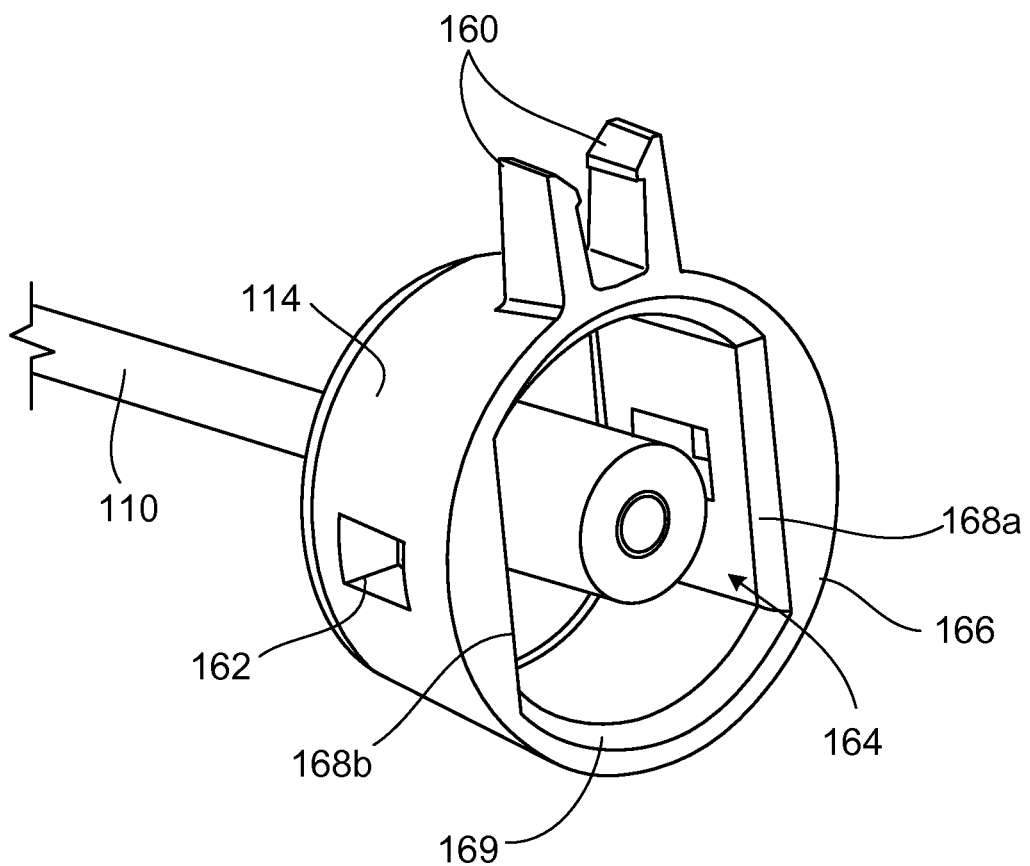

Referring to FIGS. 5A and 5B, the cover element 114 is coupled to the tubular member 110 by; for example, insert molding, welding, friction fit, or other suitable means. The cover element 114 also includes mating features 162 to engage mating features 140 of the handle 128 (FIGS. 3A and 3B), and mating feature 160 to engage the cover 126 (FIG. 1). A hollow cavity 164 extends from the proximal end 166 of the cover element 114 towards its distal end 167. The hollow cavity 164 has two straight portions 168a, 168b which engage straight portions 139a, 139b of the handle 128 and allow the handle 128 and cover element 114 to rotate together, but limit the handle 128 and cover element 114 from rotating relative to each other. The edges of the hollow cavity 164 have a chamfer 169 to provide lead-in for ease of assembly.

Figure 6:
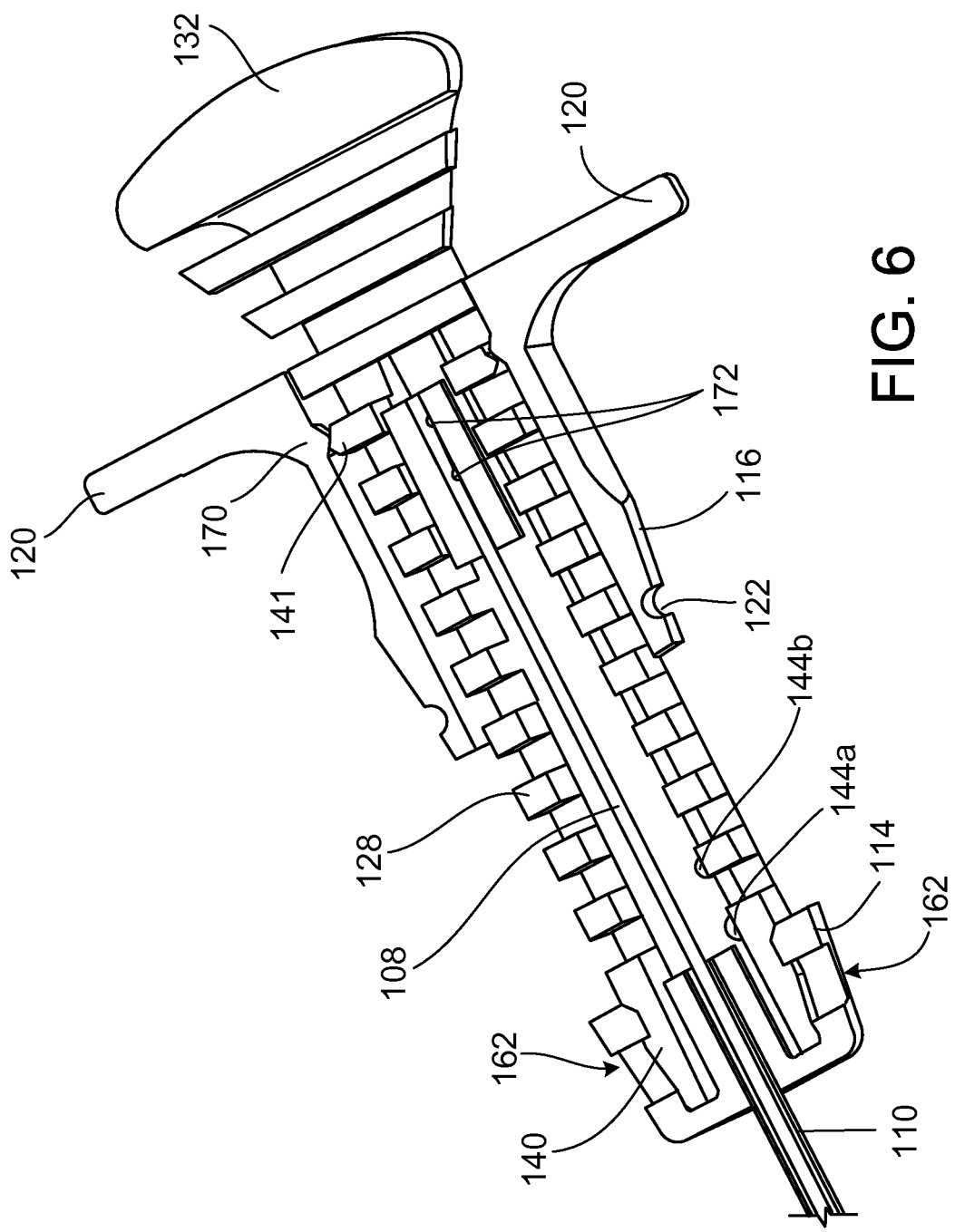
FIG. 6 is a cutaway view of the proximal portion of the delivery device of FIG. 1.

FIG. 6 is a cutaway view of the proximal end of the delivery device 100. The trigger 116 is shown pulled back towards the end of the proximal end 133 of the body 134 of the handle 128. This is considered the "fully deployed" position, as described below. When the trigger 116 reaches the fully deployed position the protrusions 170 of the trigger 116 are forced over the protrusions 141 of the handle 128. This may produce an audible snap, allowing the surgeon to easily recognize when the delivery device 100 has reached its fully deployed state.

Figure 7:
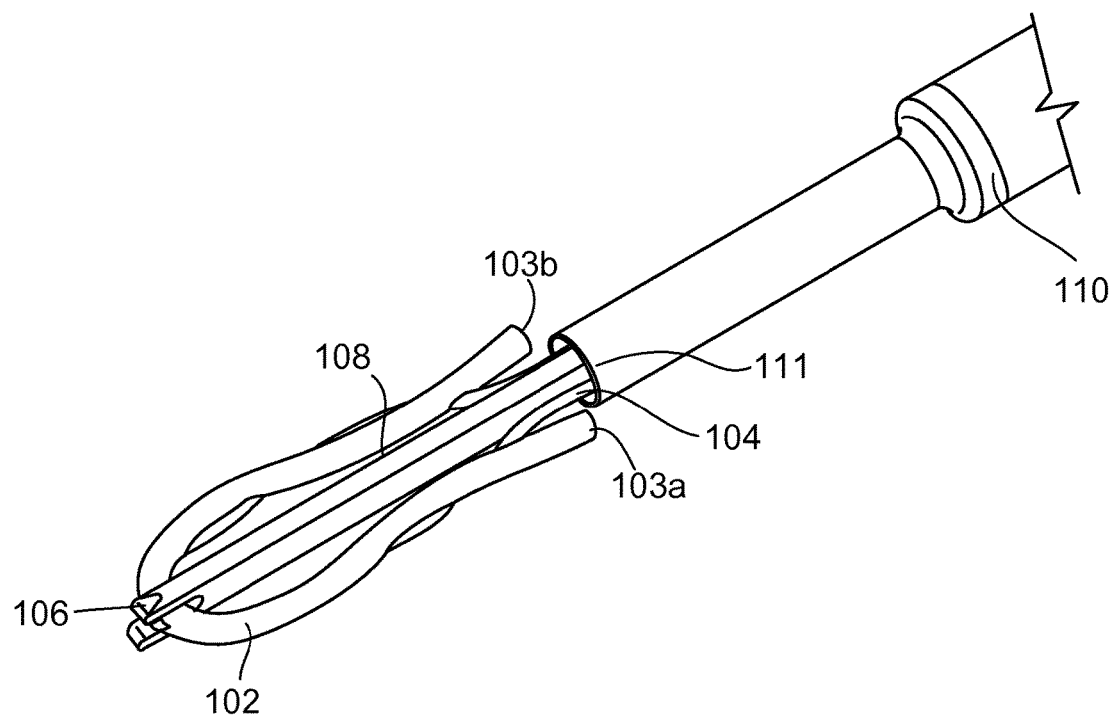
FIGS. 7-9 are perspective views of the distal end of the delivery device of FIG. 1.
Figure 9:
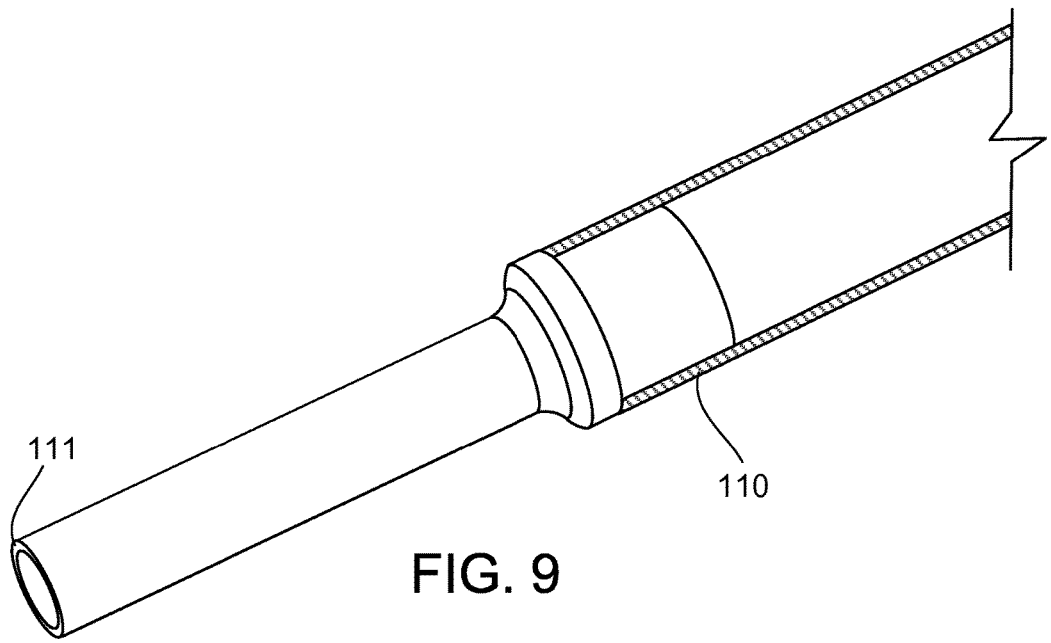
Figure 10:
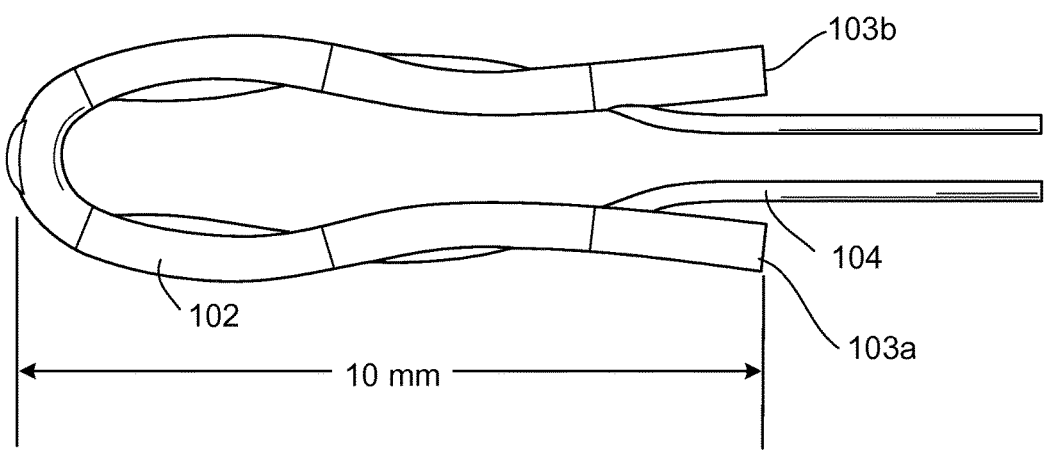
FIG. 10 is a plan view of a flexible fixation member and suture assembly.

FIGS. 7-9 show the distal end of the delivery device 100. Suture 104 is threaded through a flexible fixation member 102 bent in a general u-shape and having two terminal ends 103a, 103b (FIG. 10). The flexible fixation member 102 is formed of a malleable or flexible body. The suture 104 includes two terminal ends (not shown). One of the terminal ends is passed through the flexible fixation member 102 forming multiple curved portions of the suture 104. The suture 104 may slide with respect to the flexible fixation member 102 to form a cluster or bunch 30 including a number of folds as shown in FIG. 12C. The bunch 30 may be used to secure tissue within a surgical site as will be described in more detail below.

Portions of the suture 104 and flexible fixation member 102 are seated in a forked distal end 106 of the elongated inserter 108. The elongated inserter 108 is rectangular in cross-section but could be any types of shapes, including circular, hexagonal, triangular, polygonal, or other suitable shape. The flat sides of the elongated inserter 108 allow the suture to pass through the smaller distal end 111 of the tubular member 110 with the elongated inserter 108 without being pinched or compressed. The elongated inserter 108 transitions from a rectangular profile at the distal end 106 to a circular profile at the proximal end and mates with the tongue 156 of the trigger 116, as illustrated in FIG. 8.

Figure 11A:
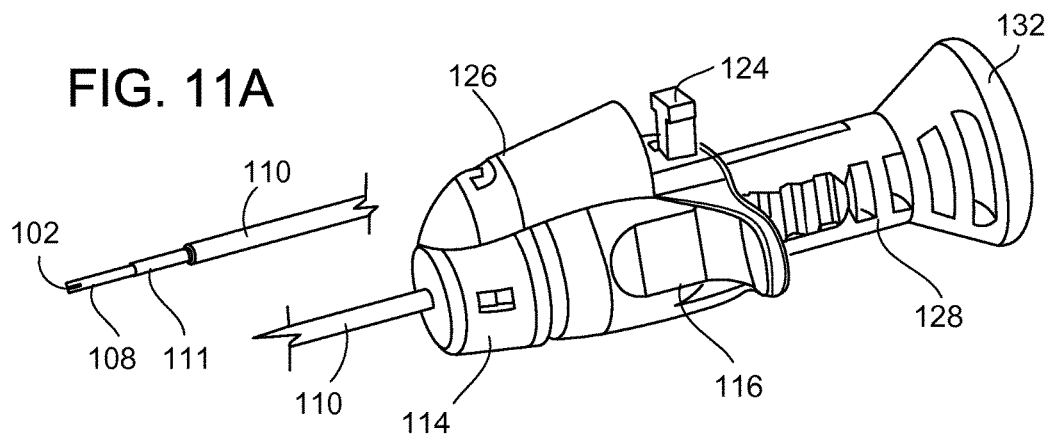
FIGS. 11A-11C illustrate the method of use of the proximal end of a delivery device.

FIGS. 11A-11C and 12A-12C illustrate a method of using the delivery device 100 of FIG. 1 to deploy a flexible fixation member 102 to below a cortical layer 204. FIG. 11A shows a delivery device 100 which is ready for use. The delivery device 100 is loaded with a flexible fixation member 102 and suture 104 assembly (FIG. 10). The suture 104 is routed through the tubular member 110 and through the delivery device 100 as described above, and then secured in retention member 151. The cover 126 hides the suture 104 that is secured in the retention member 152 to prevent premature uncleating, of the suture 104, for example, by a user pulling the suture 104 loose from the retention member 152. Referring to FIGS. 12A-12C, a hole 202 is drilled through the cortical layer 204 and into the cancellous layer 206 of bone using a drill guide 208. The distal end of the delivery device 100 is inserted into the drill guide (FIG. 12A). As the distal end of the delivery device 100 is advanced through the drill guide 208, the forked distal end 106 of the elongated inserter 108 moves the flexible fixation member 102 and suture 104 assembly past the cortical layer of bone 204 and into the cancellous layer 206 until the distal end 111 of the tubular member 110 is generally aligned with or past the bottom of the cortical layer 204, as shown in FIG. 12B. The button 124 is then depressed to allow the trigger 116 to be pulled towards the proximal end 132 of the handle 128 (FIG. 11B), pulling the elongated inserter 108 and the suture 104 back. As the trigger 116 is moved toward the proximal end 132 of the handle 128, the retention member 152 and the suture 104 secured therein become accessible. As the trigger 116 is retracted, the elongated inserter 108 is drawn up into the tubular member 110, slack in the suture 104 is taken up, and the suture 104 is tensioned. The flexible fixation member 102 is larger than the distal tip 111 of the tubular member 110. As the elongated inserter 108 and the suture 104 are drawn back, the flexible fixation member 102 begins to bunch against the distal edge 111 of the tubular member 110. When the trigger 116 is fully retracted, the flexible fixation member 102 is bunched such that it will not pull out of the hole 202 drilled in the bone. The suture 104 can then be uncleated from the retention member 152.

Figure 13A:
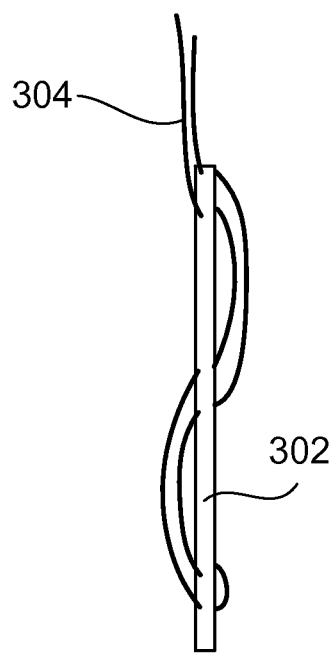
FIG. 13A is a plan view of a flexible fixation member and suture assembly.
Figure 13E:
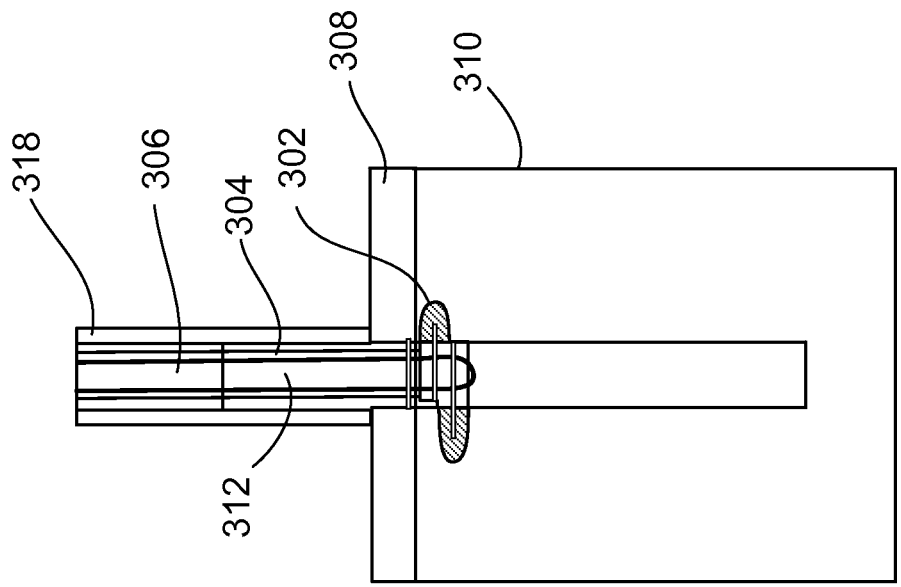
Figure 13D:
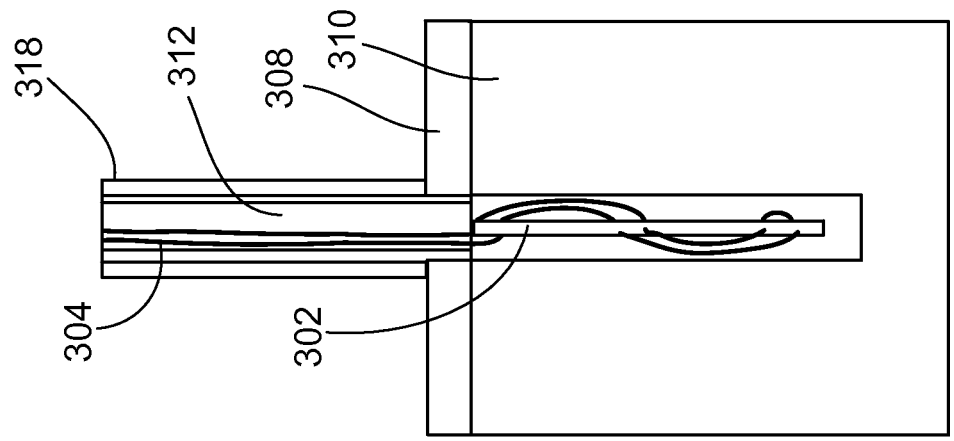
Figure 14D:
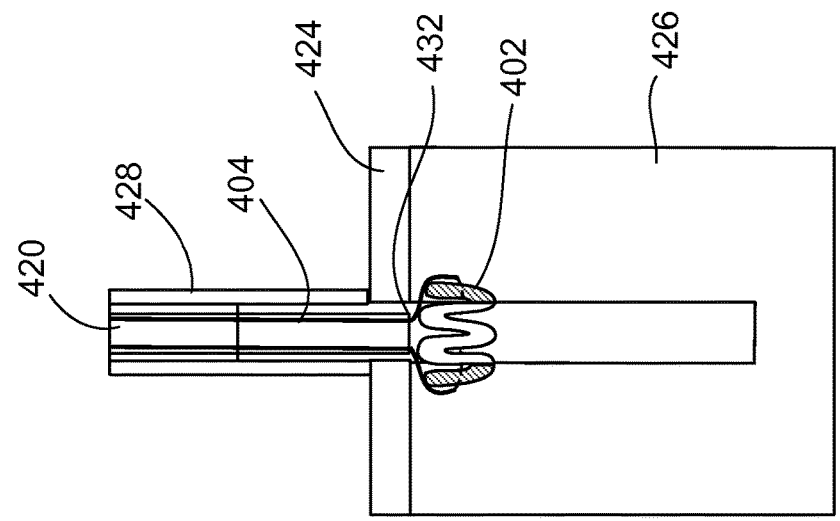
Figure 14C:
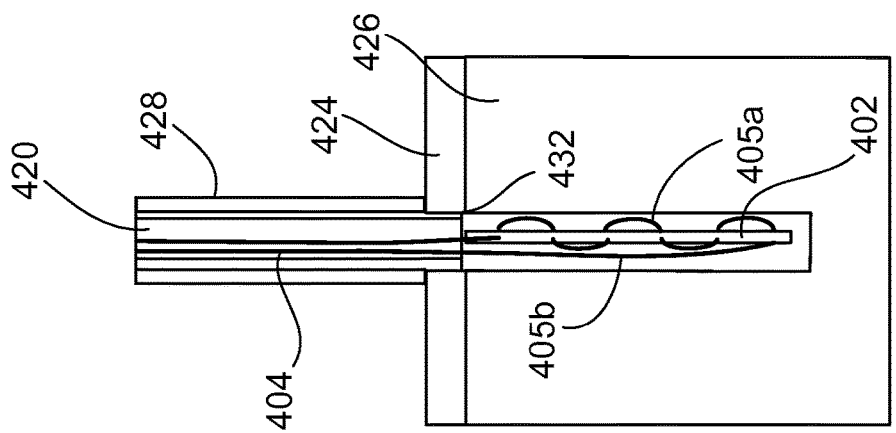
Figure 16A:
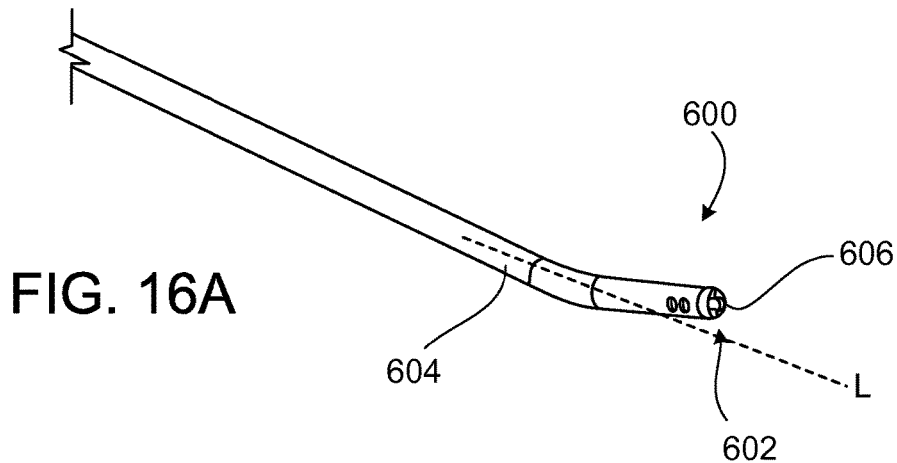
Figure 16B:
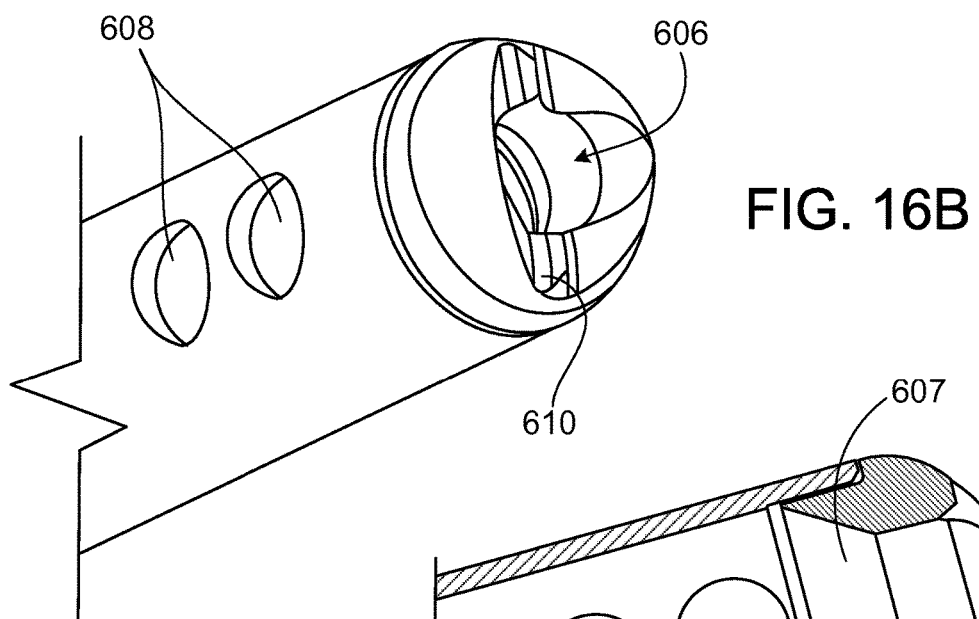
Figure 16C:
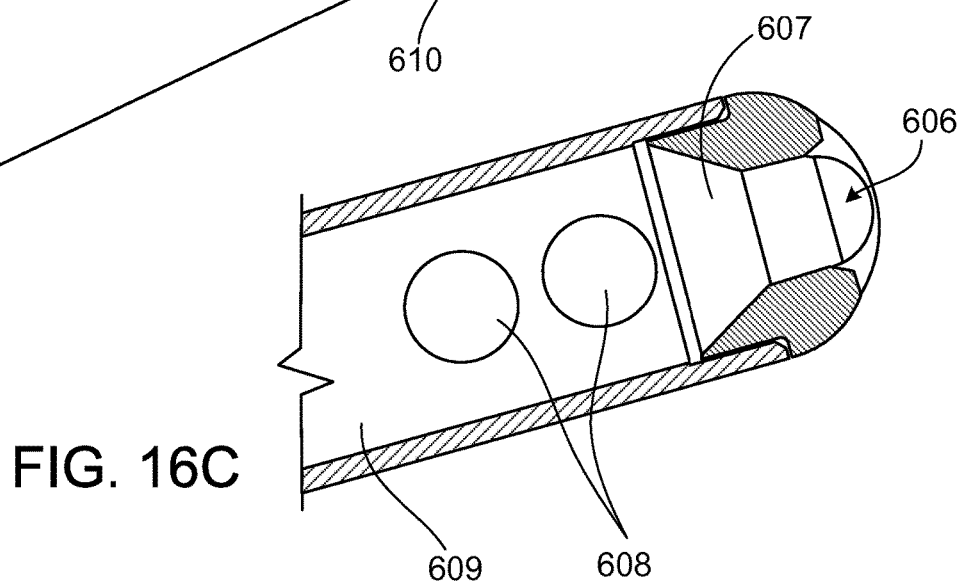
Figure 16D:
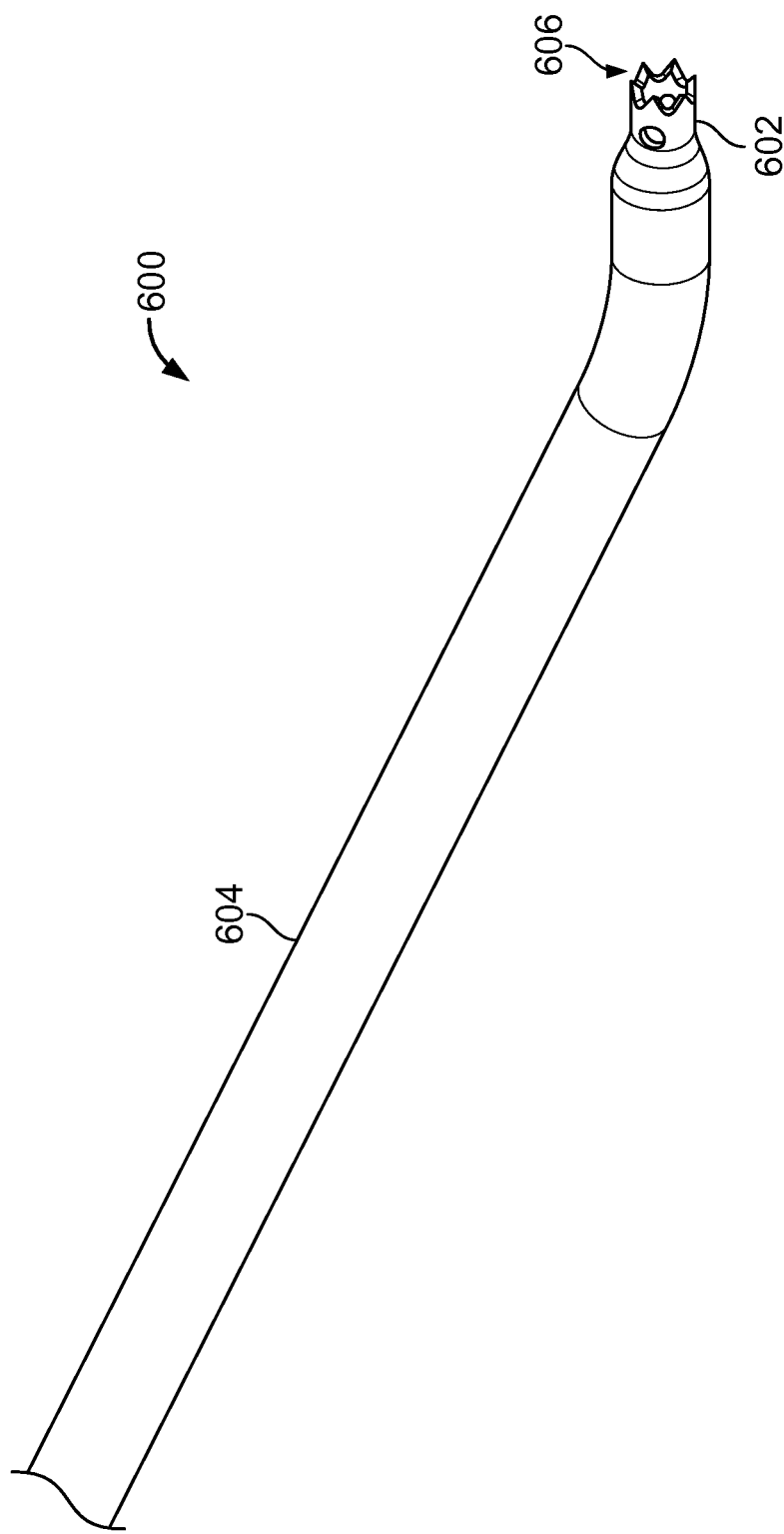
Figures 17A, 17B:
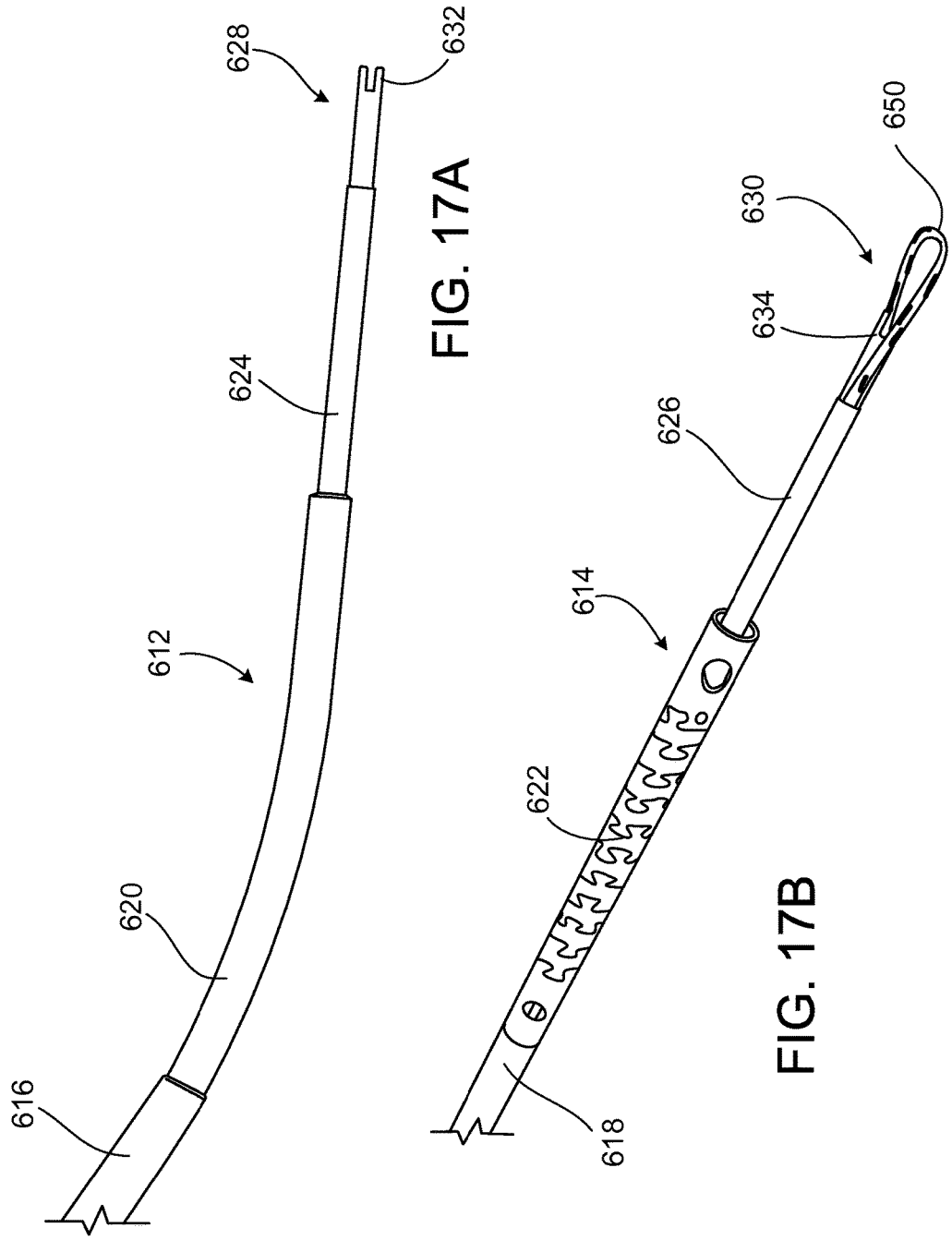
Figure 17E:
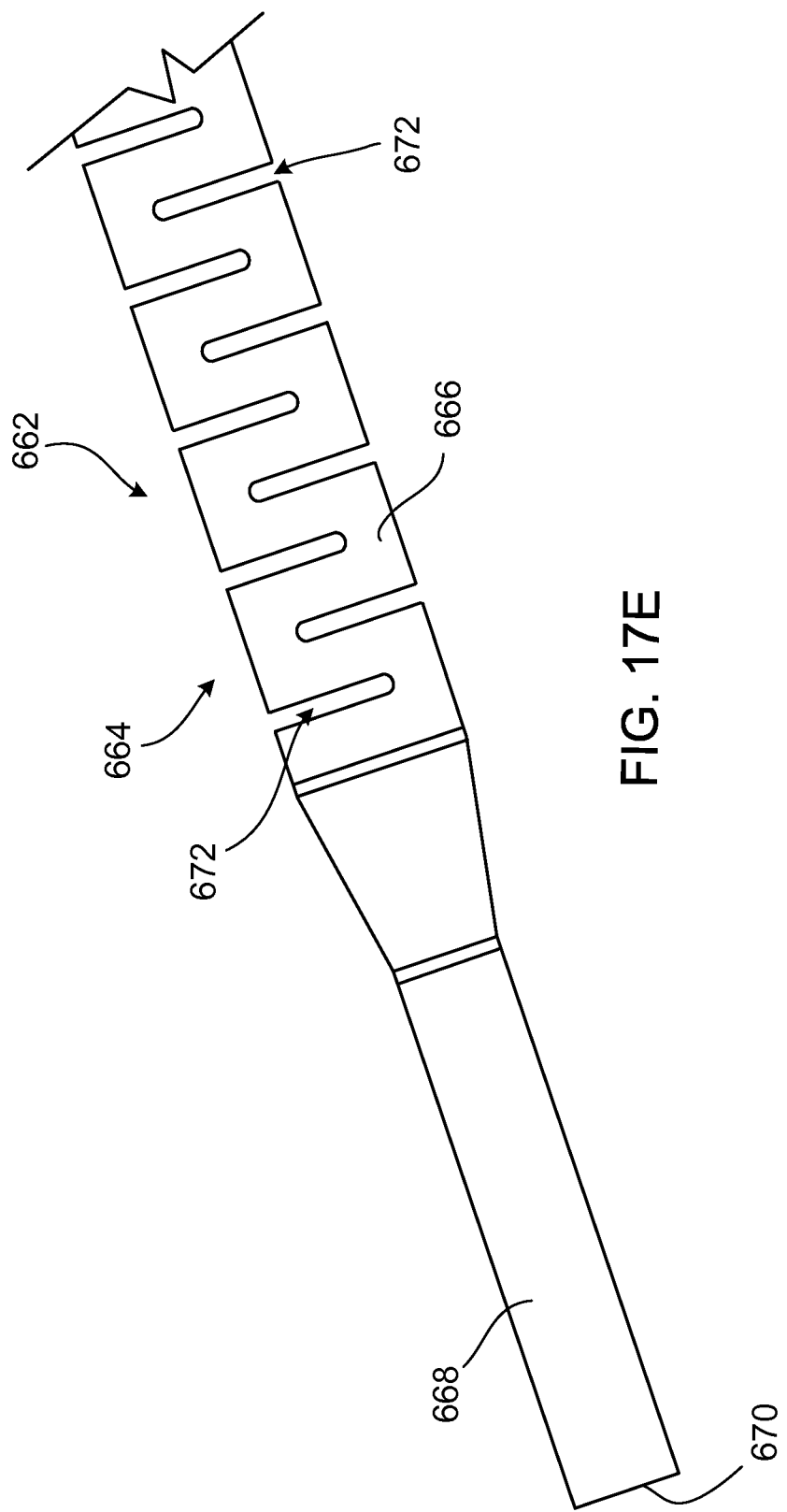

FIG. 13A is an alternative implementation of weaving the suture 304 through the flexible fixation member 302. In this implementation, the flexible fixation member 302 is not bent into a u-shape, but is substantially straight while both ends of the suture 304 are inserted in and out of the flexible fixation member 302. This implementation also includes an outer tubular member 306 which is inserted through the cortical layer 308 and into the cancellous layer 310 with the flexible fixation member 302 and suture 304 assembly. This outer tubular member 306 provides additional protection for the flexible fixation member 302 and suture 304, and prevents any pinching or other damage to the flexible fixation member 302 or suture 304 during insertion.

Figure 11B:
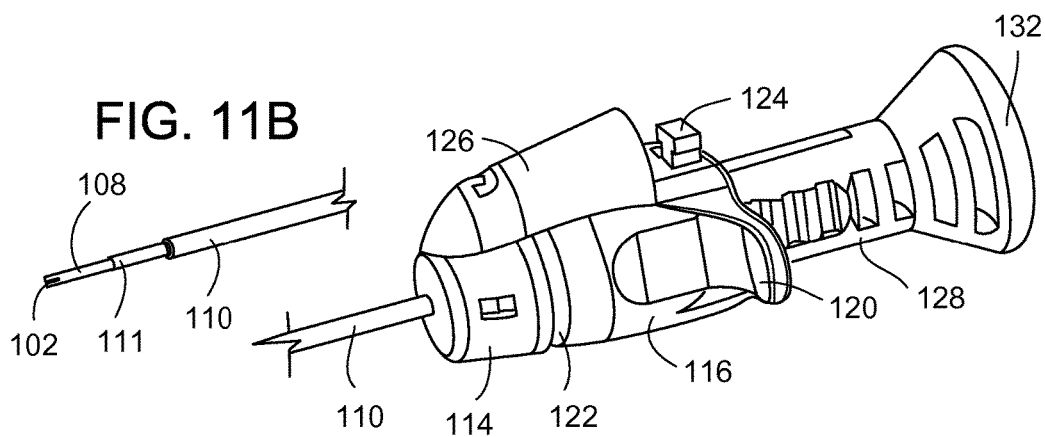
Figure 11C:
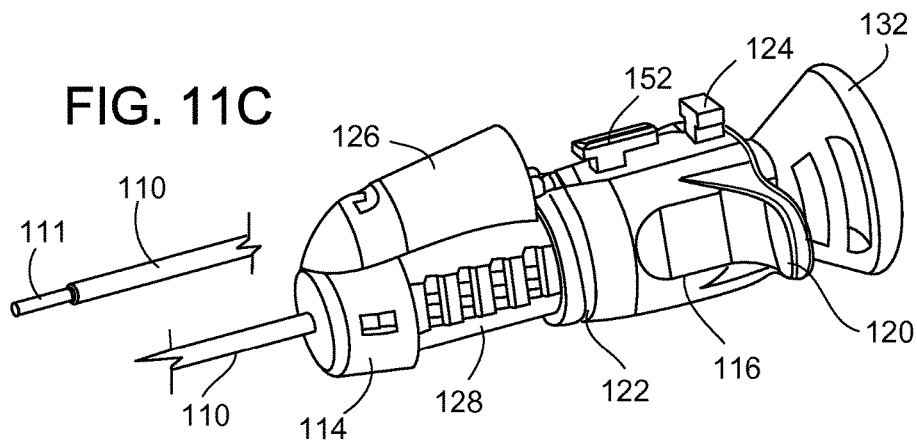

The method of delivery is similar to the method described above. The suture 304 is routed through the tubular member 312 and through the delivery device 100 as described above, and then secured in retention member 152. The cover 126 hides the suture 304 that is secured in the retention member 152 to prevent premature uncleating of the suture 304. A hole 316 is drilled through the cortical layer 308 and into the cancellous layer 310 of bone using a drill guide 318. The distal end of the delivery device 100 is inserted into the drill guide 318 (FIG. 13B). The distal end of the delivery device 100 is advanced through the drill guide 318 until the outer tubular member 306 is past the cortical layer of bone 308 and into the cancellous layer 310 and the distal edge 314 of the tubular member 312 is generally aligned with or past the bottom of the cortical layer 308, as shown in FIG. 13C. The button 124 is then depressed to allow the trigger 116 to be pulled towards the proximal end 132 of the handle 128, as shown in FIG. 11B, pulling the outer tubular member 306 and the suture 304 back. As the trigger 116 is moved toward the proximal end 132 of the handle 128, the retention member 152 and the suture 304 secured therein become accessible. The flexible fixation member 302 is larger than the distal tip 314 of the tubular member 312. As the outer tubular member 306 and the suture 304 are drawn back, the flexible fixation member 302 begins to bunch against the distal edge 314 of the tubular member 312. When the trigger 116 is fully retracted, the flexible fixation member 302 is bunched such that it will not pull out of the hole 316 drilled in the bone. The suture can then be nucleated from the retention member 152.

FIGS. 14A-14D show another implementation of the flexible fixation member 402 and suture 404. In this implementation, the flexible fixation member 402 is straight while one end 405a of the suture 404 is inserted in and out of the flexible fixation member 402 and one end 405b of the suture 404 runs parallel to the straight fixation member 402.

The method of delivery is the same method as described above with respect to FIGS. 13B-13E. The suture 404 is routed through a tubular member 420, through the delivery device 100, and secured in retention member 152. The cover 126 hides the suture 404 that is secured in the retention member 152. A hole 422 is drilled through the cortical layer 424 and into the cancellous layer 426 of bone using a drill guide 428. The distal end of the delivery device 100 is inserted into the drill guide (FIG. 14A). The distal end of the delivery device 100 is advanced through the drill guide 428 until the outer tubular member 430 is past the cortical layer of bone 424 and into the cancellous layer 426 and the distal edge 432 of the tubular member 420 is aligned with or past the bottom of the cortical layer 424, as shown in FIG. 14B. The button 124 is then depressed to allow the trigger 116 to be pulled towards the proximal end 132 of the handle 128, as shown in FIG. 11B, pulling the outer tubular member 430 and the suture 404 back. The flexible fixation member 402 is larger than the distal tip 432 of the tubular member 420. When the trigger 116 is fully retracted, the flexible fixation member 402 is bunched such that it will not pull out of the hole 422 drilled in the bone. The suture 404 can then be uncleated from the retention member 152.

FIGS. 15A-15C show another implementation of the delivery device. In this implementation, the tubular member has been omitted. The method is similar to the method described above with respect to FIGS. 11A-12C. The delivery device 100 is loaded with a flexible fixation member 502 and suture 504 assembly (FIG. 10). The suture 504 is routed through the delivery device 100 as described above, and then secured in retention member 152. The cover 126 hides the suture 504 that is secured in the retention member 152. A hole 506 is drilled in through the cortical layer 508 and into the cancellous layer 510 of bone using a drill guide 512. The distal end of the delivery device 100 is advanced through the drill guide 512 until the forked distal end 514 of the elongated inserter 516 pushes the flexible fixation member 502 and suture 504 assembly past the cortical layer of bone 508 and into the cancellous layer 510, as shown in FIG. 15B. The button 124 is then depressed to allow the trigger 116 to be pulled towards the proximal end 132 of the handle 128 (FIG. 11B), pulling the elongated inserter 516 and the suture 504 back. As the elongated inserter 516 and the suture 504 are drawn back, the flexible fixation member 502 begins to bunch against the cortical layer 508 of bone. When the trigger 116 is fully retracted, the flexible fixation member 502 is bunched such that it will not pull out of the hole 506 drilled in the bone. The suture 504 can then be uncleated from the retention member 152.

Figure 20A:
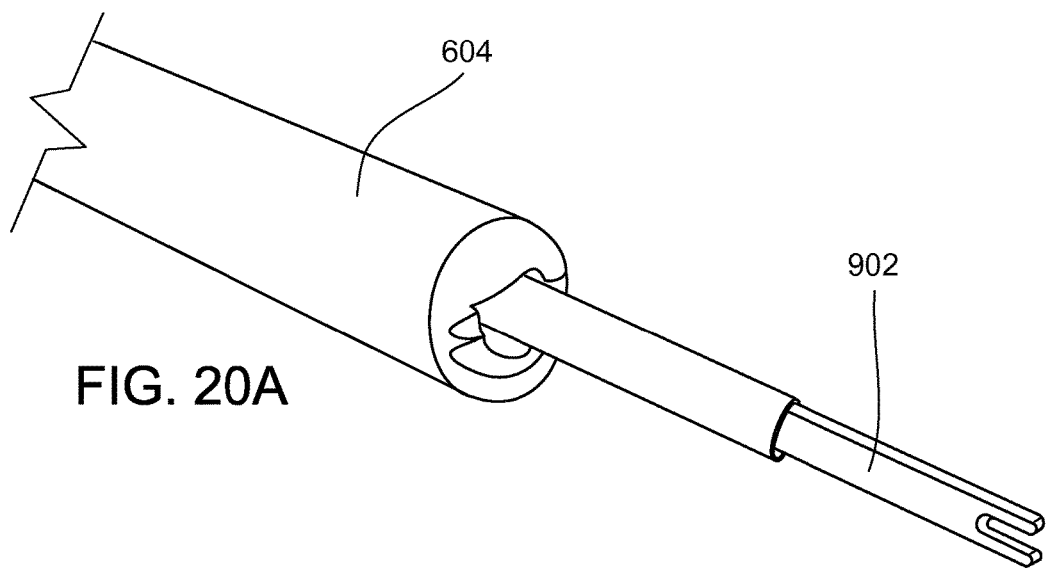
FIG. 20A is a perspective view of the distal end of an angled guide and flexible inserter.
Figure 20B:
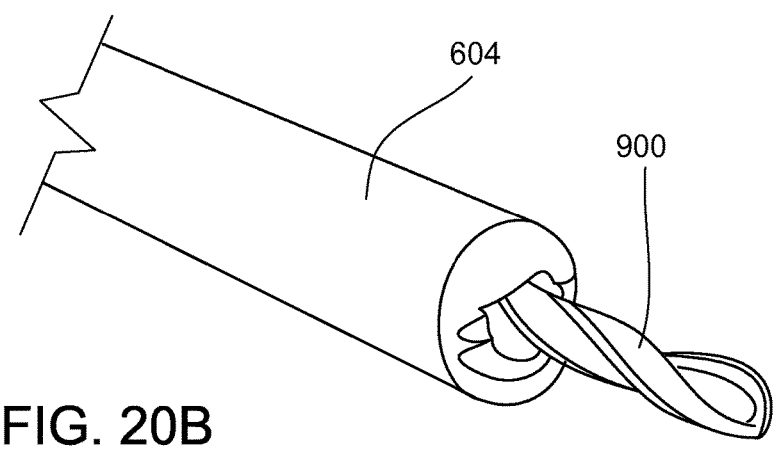
FIG. 20B is a perspective view of the distal end of an angled guide and flexible drill.

FIGS. 16A-16F show another implementation of the delivery device 600. A guide 604 includes a distal end portion 602 that is angled relative to a longitudinal axis L of the guide 604, which allows the surgeon to achieve the ideal insertion angle of, for example, a flexible drill, such as the Flexible Twist Drill for 2.3 Osteoraptor™ Curved Guide, available from Smith & Nephew, Inc. of Andover Mass., and/or a flexible suture inserter at a quicker rate, thereby reducing the potential of damage to cartilage and other tissue within the joint area. The distal end portion 602 of the guide 604 defines an opening 606 which is narrowed down via a cut or bushing 607 or swaged structure 607a placed in the distal end portion 602 (FIG. 16C, 16F) relative to the remainder of the cannula 609 of the guide 604. This narrowed portion aids in stabilizing and centering a flexible drill bit 900, 901 or a flexible inserter 902, 903 as it exits the guide 604 through the opening 606, 605, as shown in FIGS. 20A, 20B, and 20C. The distal end portion 602 also includes one or more holes 608. The holes 608 are used during surgery to view the tissue anchor and, specifically the orientation of the tissue anchor, prior to inserting the anchor into tissue, such as bone. The holes 608 may also be used to vent bone and other debris that may become located within the distal end portion 602 of the guide 604 during surgery. The distal end portion 602 of the guide 604 also includes a serrated edge 610, 611 for facilitating maintenance of the guide 604 on the bone during surgery, thereby substantially reducing slippage of the guide 604 off of the bone. Rather than a serrated edge 610, 611, the edge 610, 611 may have other features known to one of skill that would help in maintaining the guide 604 on the bone and reduce slippage. The curved guide 604 is further described in WO 2012/048050, which is incorporated herein by reference in its entirety.

FIGS. 17A through 17E illustrate exemplary implementations of a flexible elongated inserter 612, 614, 613, 615, 662, respectively, that may be used in conjunction with the guide 604 for delivering anchors, such as the suture anchors described above, into tissue. The flexible elongated inserters 612, 614, 613, 615, 662 each include an outer tubular member 616, 618, 617, 619, 664, which includes at least a flexible portion 620, 622, 621, 623, 666 and a rigid, thinned portion 624, 626, 625, 627, 668 extending to a distal end 628, 630, 629, 631, 670 of the respective inserters 612, 614, 613, 615, 662. The flexible portion 620, 622, 621, 623, 666 permits the inserter 612, 614, 613, 615, 662 to substantially conform to the shape of the guide 604 when the inserter 612, 614, 613, 615, 662 is moved through the cannula 607 or 607a of the guide 604. The flexible portion 620, 622, 621, 623, 666 may be made of a flexible material, such as, for example, nitinol or flexible plastics, or may be made from a coil cut tube (FIG. 17A), or a collection of engaging elements forming a puzzle cut tube (FIG. 17B), or a spring (FIG. 17C), or biocompatible flexible materials tube such as PEEK (FIG. 17E), or with alternating slits (N degree alternation, N=90 or 180 or other angles) (FIG. 17E), or other designs known in the art. The distal end 628, 630, 629, 631 of each of the inserters 612, 614, 613, 615 includes a pronged-end 632, 634, 633, 635, which receives a portion of a suture 650 (FIG. 17B), 651 (FIG. 17C), 652 (FIG. 17E) and a suture anchor 653 (FIG. 17C), 654 (FIG. 17D) as described above. The distal end 670 of inserter 662 may also include a pronged-end (not shown) which receives a portion of a suture and a suture anchor as described above.

Figure 18A:
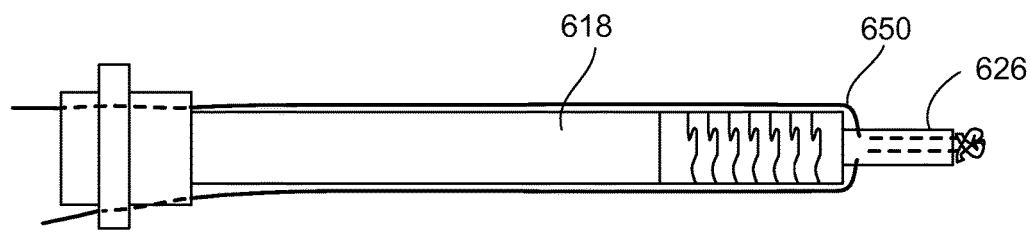
FIG. 18A is a plan view of a flexible delivery device with a suture routed externally.
Figure 18B:
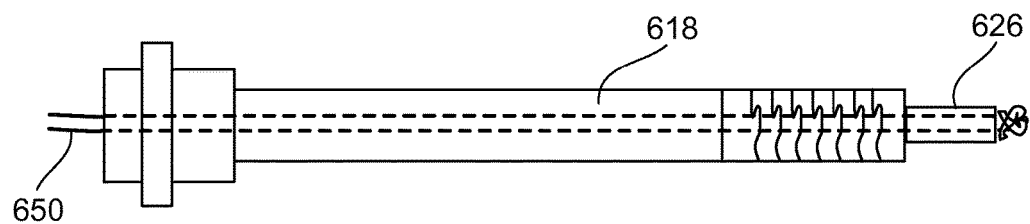
FIG. 18B is a plan view of a flexible delivery device with a suture routed internally.

Referring to FIG. 18A, the repair suture 650 may be routed through a portion of the rigid portion 626 of the outer tubular member 618 for a certain distance, and then exit the outer tubular member 618 at a point along the rigid portion 626 or flexible portion 620. Upon exit from the outer tubular member 618, the suture 650 is then routed proximally along the outside of the outer tubular member 618 and between the guide 604. This helps protect the suture from damage during use. In the alternative, as shown in FIG. 18B, the repair suture 650 may be routed proximally within the outer tubular member 618. The same suture routing method is applicable to all the inserter options shown in FIG. 17.

The method of use of delivery device 600 is similar to the method described above with respect to FIGS. 11A-12C. The curved guide 604 is placed against the cortical layer of tissue. The flexible drill 900 is delivered through the curved guide 604 and used to form a hole in the bone below the cortical layer. Once the hole is formed, the flexible drill 900 is removed from the guide 604 and the flexible inserter 902 is inserted through the guide 604. As described above, the repair suture and suture anchor are preloaded onto the forked end of the flexible inserter 902. The flexible inserter 902 is advanced through the guide 604 past the cortical layer of bone and into the cancellous layer. The flexible elongated inserter 902 is then retracted and the suture anchor is bunched such that it will not pull out of the hole drilled in the boric, as described with respect to FIGS. 11A-12C.

Figure 19A:
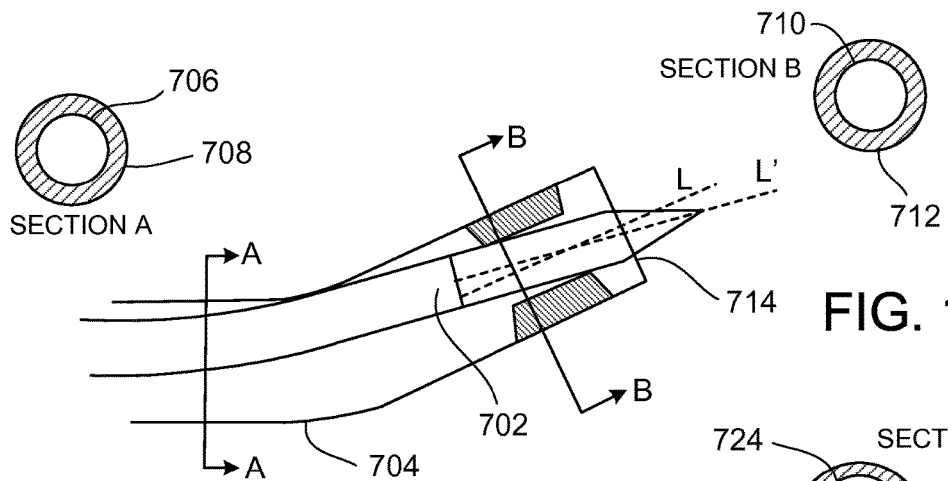
FIGS. 19A-19C are plan views of angled guides and a flexible drill or inserter.
Figure 19B:
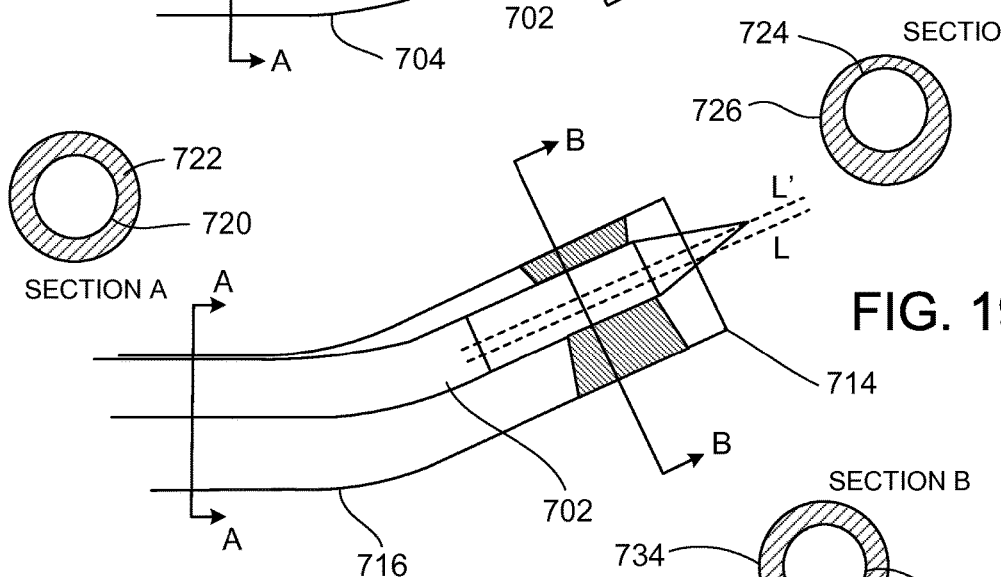
Figure 19C:
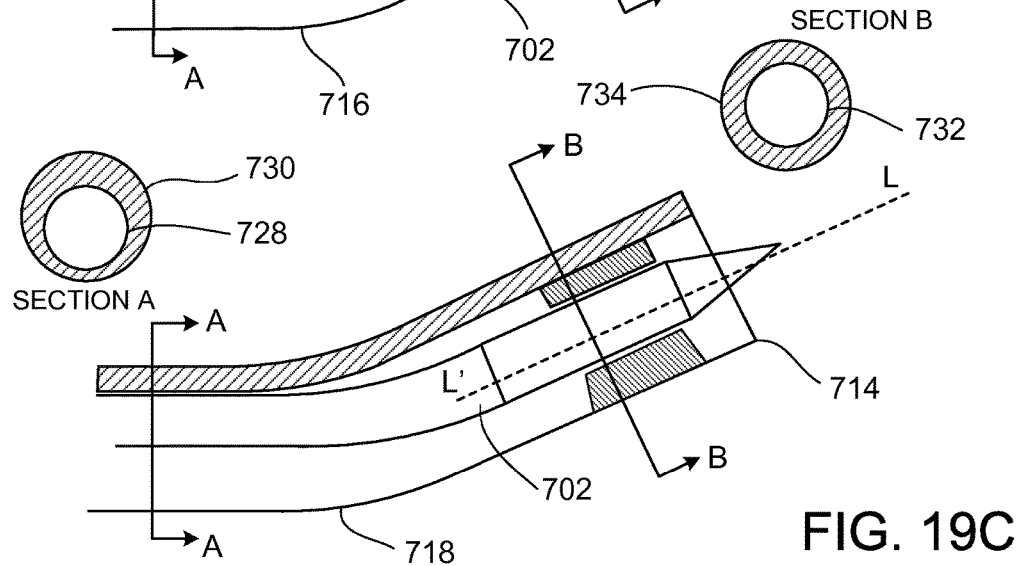

As discussed above, the distal end portion 602 of the guide 604 defines an opening 606 which narrows down via a cut or bushing 607 placed in the distal end portion 602 (FIG. 16C) relative to the remainder of the cannula 609 of the guide 604. This narrowed portion aids in stabilizing and centering a flexible drill bit 900 or a flexible inserter 902 as it exits the guide 604. FIGS. 19A-19C illustrate additional implementations for assisting in the centering of the drill bit or inserter trajectory from the guide 604. As shown in FIG. 19A, a flexible drill or inserter 702 is inserted within a curved guide 704. The curved guide 704 has a first inner diameter (ID 706, which is concentric with a first outer diameter (OD) 708 as taken along line A-A of FIG. 19A. The guide 704 has a second ID 710, which is concentric with a second OD 712 as taken along line B-B of FIG. 19A. In this implementation, the longitudinal axis L' of the drill or inserter 702 may be angularly offset from the longitudinal axis L of the distal end 714 of the curved guide 704 because the drill or inserter 702 tends to remain straight.

FIGS. 19B and 19C show implementations of angled guides 716, 718 that aid in aligning the longitudinal axes L, L' of the flexible drill or inserter 702 and the guide 716, 718. FIG. 19B shows a guide 716 with a first ID 720, which is concentric with a first OD 722 as taken along line A-A of FIG. 19B, and a second ID 724, which is eccentric with respect to a second OD 726 taken along line B-B of FIG. 19B. The second ID 724 is offset toward the inside of the guide 716. The offset second ID 724 brings the longitudinal axis L' of the distal end of the drill or inserter 702 into substantial angular alignment with the longitudinal axis L of the distal end of the guide 716. FIG. 19C shows a guide 718 with a first ID 728, which is eccentric with respect to a first OD 730 as taken along line A-A of FIG. 19C, and a second ID 732, which is concentric with a second OD 734 taken along line B-B of FIG. 19C. The first ID 728 is offset toward the outside of the guide 718. The offset first ID 728 brings the longitudinal axis L' of the distal end of the drill or inserter 702 into alignment with the longitudinal axis L of the distal end of the guide 718. In addition to aligning the longitudinal axes L, L', the offset IDs and ODs may allow the device to support higher loads. For example, when bent, the concave side of the bent drill or inserter 702 supports the compressive or tensional loads. Thus, by thickening the wall of the concave side, more load may be supported.

A number of implementations have been described. Nevertheless, it will be understood that various modifications may be made without departing from the spirit and scope of the disclosure. For example, the fixation members and the flexible members may include a growth factor, such as, for example, an angiogenic factor. The fixation members and the flexible members may also be loaded with a bioactive material, a stimulant, or any substance that promotes healing of the tissue. In addition, the handle may include more than one cut out portion to allow the trigger to be secured at different places along the body of the handle. Moreover, the hollow cavity of the cover element may have more than two straight portions, one straight portion, or no straight portions. Elements 146 and 148 have been described as slots, but may be through holes or other shapes.

In addition, although the elongated inserter has been described as having a rectangular profile at its distal end and a circular profile at its proximal end, other profile combinations, as well as constant profiles are contemplated.

Moreover, in addition to the particular materials described, the elements of the delivery device may be made from other suitable materials. For example, the handle may be injection molded and made of polycarbonate. Accordingly, other implementations are within the scope of the following claims.

What is claimed is:
1. An assembly comprising:
a flexible fixation member comprising a body having two terminal ends;
a suture interwoven through the fixation member along a length of the fixation member body between the terminal ends such that portions of the fixation member are slidable relative to the suture;
a delivery device comprising:
a first tubular member; and
an elongated inserter slidably disposed within the first tubular member, the inserter comprising a proximal end and a distal end, the distal end configured to engage the flexible fixation member and the suture;
an elongated handle extending between a proximal end and a distal end, the handle including a hollow body and a longitudinal slot extending from the distal end; and
a trigger extending from a proximal end to a distal end, the trigger including:
a trigger cannulation extending from the proximal end to the distal end of the trigger; and
a tongue extending within the trigger cannulation;
wherein the handle is received within the trigger cannulation such that the tongue of the trigger fits through the longitudinal slot of the handle;
wherein the trigger is slideable with respect to the handle to proximally retract; and
wherein the elongated inserter and suture are actuatable to proximally retract the inserter relative to the first tubular member such that the fixation member bunches against a distal end of the first tubular member.

2. The assembly of claim 1, wherein the proximal end of the inserter is attached to the tongue of the trigger such that the inserter moves with the trigger.

3. The assembly of claim 1, wherein the delivery device further comprises a cover element coupled to the distal end of the handle, wherein a proximal end of the first tubular member is coupled to the cover element.

4. The assembly of claim 3, wherein the cover element and the handle are rotationally and axially coupled.

5. The assembly of claim 3, further comprising:
a retention member mounted to an outer surface of the trigger and adapted to secure a proximal end portion of the suture thereto; and
a cover mounted to the cover element and including a hollow body dimensioned to receive the retention member therein.

6. The assembly of claim 5, wherein the trigger is slidable from a first longitudinal position, where the retention member is hidden by the cover and a second longitudinal position, proximal to the first longitudinal position, where the retention member is not hidden by the cover.

7. The assembly of claim 1, wherein the first tubular member and the inserter are dimensioned such that a portion of the suture extending proximally from the flexible fixation member is routable through the first tubular member concurrently with the inserter without being compressed.

8. The assembly of claim 1, wherein the distal end of the inserter is forked.

9. The assembly of claim 8, wherein a diameter of the first tubular member is less than a lateral span of the flexible fixation member when mounted to the inserter.

10. The assembly of claim 1, wherein the flexible fixation member includes a bend and wherein the distal end of the inserter engages at least a portion of the bend.

11. An assembly comprising:
a flexible fixation member comprising a body having two terminal ends;
a suture passing through the flexible fixation member at various points along a length of the body between the terminal ends such that portions of the fixation member are slidable relative to the suture and configurable to form a cluster within a surgical site;
a delivery device comprising:
an elongated inserter comprising a distal end and a proximal end, the distal end configured to receive a portion of the flexible fixation member and the suture therein; and
a handle including a hollow body and a longitudinal slot extending from a distal end; and
a finger-engageable trigger slidably mounted to the handle and fixedly coupled to the proximal end of the inserter, the trigger configured to advance and retract the inserter relative to the handle, the trigger comprising:
a retention member for retaining a proximal end portion of the suture;
a trigger cannulation extending from a proximal end to a distal end of the trigger; and
a tongue extending within the trigger cannulation;
wherein the handle is received within the trigger cannulation such that the tongue of the trigger fits through the longitudinal slot of the handle.

12. The assembly of claim 11, wherein the distal end of the inserter is forked.

13. The assembly of claim 11, wherein the flexible fixation member includes a bend and wherein the distal end of the inserter engages at least a portion of the bend.

14. The assembly of claim 11, further comprising:
a cover element coupled to the distal end of the handle; and
a cover mounted to the cover element and including a hollow body dimensioned to receive the retention member therein.

15. The assembly of claim 11, wherein the trigger is slidable from a first longitudinal position, where the retention member is hidden by the cover and a second longitudinal position, proximal to the first longitudinal position, where the retention member is not hidden by the cover.

16. The assembly of claim 11, wherein the proximal end of the inserter is attached to the tongue of the trigger such that the inserter moves with the trigger.

* * * * *